US007492934B2

(12) United States Patent
Mundy et al.

(10) Patent No.: US 7,492,934 B2
(45) Date of Patent: Feb. 17, 2009

(54) METHODS AND APPARATUS FOR MODEL-BASED DETECTION OF STRUCTURE IN VIEW DATA

(75) Inventors: Joseph L. Mundy, Barrington, RI (US); Benjamin Kimia, Providence, RI (US)

(73) Assignee: Brown University, Providence, RI (US)

( * ) Notice: Subject to any disclaimer, the term of this patent is extended or adjusted under 35 U.S.C. 154(b) by 784 days.

(21) Appl. No.: 10/871,265

(22) Filed: Jun. 17, 2004

(65) Prior Publication Data

US 2004/0267114 A1 Dec. 30, 2004

Related U.S. Application Data

(60) Provisional application No. 60/479,114, filed on Jun. 17, 2003.

(51) Int. Cl.
*G06K 9/00* (2006.01)
(52) U.S. Cl. ........................ 382/128; 382/100
(58) Field of Classification Search ................ 382/100, 382/128
See application file for complete search history.

(56) References Cited

U.S. PATENT DOCUMENTS

| 5,699,799 | A | * | 12/1997 | Xu et al. ................ 600/407 |
| 5,712,803 | A | * | 1/1998 | Garuet-Lempirou ........ 702/158 |
| 5,769,640 | A | | 6/1998 | Jacobus et al. ............ 434/262 |
| 5,921,920 | A | | 7/1999 | Marshall et al. ........... 600/300 |
| 5,966,141 | A | * | 10/1999 | Ito et al. .................. 345/473 |
| 6,028,907 | A | * | 2/2000 | Adler et al. ................. 378/4 |

(Continued)

FOREIGN PATENT DOCUMENTS

WO    WO-02/31768 A2    4/2002

(Continued)

OTHER PUBLICATIONS

Frangi et al., "Model-Based Quantization of 3-D Magnetic Resonance Angiographic Images", IEEE Transactions on Medical Imaging, vol. 18 No. 10 Oct. 1999 p. 946-956.*

(Continued)

*Primary Examiner*—Samir A Ahmed
*Assistant Examiner*—Gandhi Thirugnanam
(74) *Attorney, Agent, or Firm*—Wolf, Greenfield & Sacks, P.C.

(57) ABSTRACT

In one aspect, a method and apparatus for determining a value for at least one parameter of a configuration of a model associated with structure of which view data has been obtained including detecting at least one feature in the view data, and determining the value for the at least one parameter of the configuration of the model based at least in part on the at least one feature. In another aspect, a method and apparatus for detecting at least one blood vessel from object view data obtained from a scan of the at least one blood vessel including generating a model of the at least one blood vessel, the model having a plurality of parameters describing a model configuration, determining a hypothesis for the model configuration based, at least in part, on at least one feature detected in the object view data, and updating the model configuration according to a comparison with the object view data to arrive at a final model configuration, so that the final model configuration represents the at least one blood vessel.

32 Claims, 18 Drawing Sheets

U.S. PATENT DOCUMENTS

| | | | | |
|---|---|---|---|---|
| 6,236,878 | B1 | 5/2001 | Taylor et al. | 600/416 |
| 6,409,760 | B1 | 6/2002 | Melvin | 623/3.1 |
| 6,434,265 | B1 * | 8/2002 | Xiong et al. | 382/154 |
| 6,501,848 | B1 | 12/2002 | Carroll et al. | 382/128 |
| 6,507,633 | B1 * | 1/2003 | Elbakri et al. | 378/8 |
| 6,915,004 | B2 * | 7/2005 | Newport et al. | 382/131 |
| 7,043,290 | B2 * | 5/2006 | Young et al. | 600/416 |
| 7,257,237 | B1 * | 8/2007 | Luck et al. | 382/103 |
| 2002/0142294 | A1 | 10/2002 | Blair et al. | 435/5 |
| 2003/0053697 | A1 * | 3/2003 | Aylward et al. | 382/203 |
| 2003/0076987 | A1 * | 4/2003 | Wilson et al. | 382/128 |
| 2003/0099391 | A1 | 5/2003 | Bansal et al. | 382/131 |
| 2003/0187358 | A1 | 10/2003 | Okerlund et al. | 600/443 |
| 2004/0267114 | A1 * | 12/2004 | Mundy et al. | 600/427 |
| 2006/0182327 | A1 * | 8/2006 | Mundy et al. | 382/132 |

FOREIGN PATENT DOCUMENTS

WO    WO 02/31768 A2    4/2002

OTHER PUBLICATIONS

European Office Action dated Jun. 27, 2006.
"A synchrotron radiation microtomograph system for the analysis of trabecular bone samples", Murielle Salome et al., Am. Assoc. Phys. Med., Med. Phys. 26(10), Oct. 1999, pp. 2194-2204.
"Curves: Curve Evolution for Vessel Segmentation", Liana M. Lorigo et al., Medical Image Analysis, 2001, pp. 1-14.
"Resection Proposals for Oncologic Liver Surgery based on Vascular Territories", B. Preim et al., CARS/Springer 2002, pp. 1-6.
"Computer-Assisted Visualization of Arteriovenous Malformations on the Home PC", Elizabeth Bullitt et al., Neurosurgery 48:576-583, 2001.

* cited by examiner

METHODS AND APPARATUS FOR MODEL-BASED DETECTION OF STRUCTURE IN VIEW DATA

RELATED APPLICATIONS

This application claims the benefit under 35 U.S.C. §119 (e) of U.S. Provisional Application No. 60/479,114, filed Jun. 17, 2003, entitled "MODEL-BASED TOMOGRAPHIC RECONSTRUCTION OF VESSEL NETWORKS," by Mundy et al., which is incorporated by reference herein in its entirety.

FIELD OF THE INVENTION

The present invention relates to imaging and more particularly to model-based techniques for detecting structure in view data, for example, in view data obtained from an X-ray scanning device.

BACKGROUND OF THE INVENTION

X-ray imaging technology provides a non-invasive technique of visualizing the internal structure of an object of interest by exposing the object to high energy electromagnetic radiation (i.e., X-rays). X-rays emitted from a radiation source pass through the object and are absorbed at varying levels by the internal structures of the object. As a result, X-ray radiation exiting the object is attenuated according to the various absorption characteristics of the materials which the X-rays encounter. By measuring the attenuation of the X-ray radiation that exits the object, information related to the density distribution of the object may be obtained.

To obtain X-ray information about an object, an X-ray source and an array of detectors responsive to X-ray radiation may be arranged about the object. Each detector in the array, for example, may generate an electrical signal proportional to the intensity of X-ray radiation impinging on a surface of the detector. The source and array may be rotated around the object in a circular path to obtain a number of views of the object at different angles. At each view, the detector signal generated by each detector in the array indicates the total absorption (i.e., attenuation) incurred by material substantially in a line between the X-ray source and the detector. Therefore, the array of detection signals records the projection of the object onto the detector array at a number of views of the object, and provides one method of obtaining view data of the object.

View data obtained from an X-ray scanning device may be of any form that provides attenuation information (e.g., detector outputs) as a function of view angle or orientation with respect to the object being imaged. View data may be obtained by exposing a planar cross-section of the object, referred to as a slice, to X-ray radiation. Each rotation about the object (e.g., a 180 degree rotation of the radiation source and detector array) provides attenuation information about a two-dimensional (2D) slice of the object.

Accordingly, the X-ray scanning process transforms a generally unknown density distribution of an object into view data corresponding to the unknown density distribution. FIG. 1A illustrates a diagram of the transformation operation performed by the X-ray scanning process. A 2D cross-section of object 100 having an unknown density distribution in object space is subjected to X-ray scanning. Object space refers herein to the coordinate frame of an object of interest, for example, an object undergoing an X-ray scan. A Cartesian coordinate frame (i.e., (x, y, z)) may be a convenient coordinate system for object space, however, object space may be described by any other suitable coordinate frame, such as spherical or cylindrical coordinates.

X-ray scanning process 110 generates object view data 105 in a view space coordinate frame (e.g., coordinate frame $(t,\theta)$). For example, object view data 105 may include attenuation information from a plurality of detectors in an array (corresponding to the view space axis $t_i$), at a number of orientations of the X-ray scanning device (corresponding to the view space axis $\theta_i$). Accordingly, X-ray scanning process 110 transforms a continuous density distribution in object space to discrete view data in view space.

To generate an image of the 2D density distribution from view data of an object, the view data may be projected back into object space. The process of transforming view data in view space into image data represented in object space is referred to as image reconstruction. FIG. 1B illustrates an image reconstruction process 120 that transforms view data 105 into a 2D image 100' (e.g., a viewable image of the cross-section of object 100 that was scanned). To form 2D image 100', a density value for each discrete location of the cross-section of object 100 in object space is determined based on the information available in view data 105.

Many techniques have been developed for image reconstruction to transform acquired view data into image data. For example, filtered back-projection is a widely used technique to form 2D images from view data obtained from an X-ray scanning device. In addition, a number of such 2D images taken across successive slices of an object of interest may be stacked together to form a three dimensional (3D) image. In medical imaging, computed tomography (CT) images may be acquired in this manner.

Images obtained via reconstruction contain less information than the view data from which they were computed. The loss in information is due in part to the discrete nature of X-ray scanning (i.e., a finite number of detectors and a finite number of views) and to assumptions made during back-projection. In this respect, an image represents intensity as a discrete function of space. The term "intensity" refers generally to a magnitude, degree and/or value at some location in the image. To back-project view data, the scan plane (i.e., the 2D cross-section of the object being imaged) may be logically partitioned into a discrete grid of pixel regions.

Each pixel region in object space may be assigned an intensity value from a finite number of integral attenuation measurements taken along rays intersecting the region of space corresponding to the respective pixel region. That is, intensity values are assigned such that the discrete sum of assigned intensities along rays through the grid match the corresponding integral attenuation measurements. This operation assumes that all structure within a pixel region has a same and single density and therefore computes an average of the density values within the corresponding region of space. This averaging blurs the image and affects the resulting image resolution.

When multiple structures are sampled within a single pixel (e.g., when structure within the object is smaller than the dimension of the corresponding pixel region and and/or the boundary of a structure extends partially into an adjacent pixel region), information about the structure is lost. The result is that the reconstructed image data has less resolution than the view data from which it was generated. This loss of resolution may obscure and/or eliminate detail in the reconstructed image.

In conventional medical imaging, a human operator, such as a physician or diagnostician, may visually inspect a reconstructed image to make an assessment, such as detection of a tumor or other pathology or to otherwise characterize the internal structures of a patient. However, this process may be difficult and time consuming. For example, it may be difficult to assess 3D biological structure by attempting to follow 2D structure through a series of stacked 2D images. In particular, it may be perceptually difficult and time consuming to understand how 2D structure is related to 3D structure as it appears, changes in size and shape, and/or disappears in successive 2D image slices. A physician may have to mentally arrange hundreds or more 2D slices into a 3D picture of the anatomy. To further frustrate this process, when anatomical structure of interest is small, the structure may be difficult to discern or absent altogether in the reconstructed image.

Image processing techniques have been developed to automate or partially automate the task of understanding and partitioning the structure in an image and are employed in computer aided diagnosis (CAD) to assist a physician in identifying and locating structure of interest in a 2D or 3D image. CAD techniques often involve segmenting the image into groups of related pixels and identifying the various groups of pixels, for example, as those comprising a tumor or a vessel or some other structure of interest. However, segmentation on reconstructed images has proven difficult and Applicant has appreciated that it may be ineffective in detecting small structures whose features have been obscured or eliminated during image reconstruction.

Reconstructed images of view data obtained from conventional X-ray scanning devices may be limited to a resolution of approximately 500 microns. As a result, conventional imaging techniques may be unable to image structure having dimensions smaller than 500 microns. That is, variation in the density distribution of these small structures cannot be resolved by conventional image reconstruction. Micro-computer tomography (microCT) can produce view data of small objects at resolutions that are an order of magnitude greater than conventional X-ray scanning devices. However, microCT cannot image large objects such as a human patient and therefore is unavailable for in situ imaging of the human anatomy.

Model-based techniques have been employed to avoid some of the problems associated with image reconstruction and post-reconstruction image processing algorithms. Model-based techniques may include generating a model to describe structure assumed to be present in the view data of an object of interest. For example, a priori knowledge of the internal structure of an object of interest may be used to generate the model. The term "model" refers herein to any geometric, parametric or other mathematical description and/ or definition of properties and/or characteristics of a structure, physical object, or system. For example, in an X-ray environment, a model of structure may include a mathematical description of the structure's shape and density distribution. A model may include one or more parameters that are allowed to vary over a range of values, such that the model may be deformed to take on a variety of configurations. The term "configuration" with respect to a model refers herein to an instance wherein each of the model parameters has been assigned a particular value.

Once a configuration of a model is determined, view data of the model (referred to as model view data) may be computed, for example, by taking the radon transform of the model. The radon transform, operating on a function, projects the function into view space. FIG. 1C illustrates the operation of the radon transform 130 on a model 125 of object 100. Model 125 is described by the function $f(\Phi)$ in model space, where $\Phi$ is a vector of the parameters characterizing the model. Since model 125 is generated to describe object 100, it may be convenient to use the same coordinate frame for model space and object space, although they may be different so long as the transformation between the two coordinate frames are known. The radon transform 130 transforms model 125 from model space to model view data 105' (i.e., to a function $\tilde{g}_i$ in the view space coordinate frame).

It should be appreciated that X-ray scanning process 110 and radon transform 130 perform substantially the same operation, i.e., both perform a transformation from object space (or model space) to view space. The scanning process performs a discrete transformation from object space to view space (i.e., to a discrete function in $(\theta_i, t_i)$) and the radon transform performs a continuous transformation from object space to view space (i.e., to a continuous function in $(\theta, t)$). Model view data obtained by projecting a configuration of the model (i.e., an instance of $f$ where each parameter in $\Phi$ has been assigned a value) into view space via the radon transform, may then be compared to the object view data acquired from the X-ray scanning device to measure how accurately the model describes the structure of interest in the object being scanned. The model may then be deformed or otherwise updated until its radon transform (the model view data) satisfactorily fits the object view data, i.e., until the configuration of the model has been optimized. The optimization may be formulated, for example, by assuming that the observed object view data arose from structure that is parameterized as the model and finding the parameterization that best describes the object view data. For example, model deformation may be guided by minimizing the expression:

$$E(\Phi) = \int_N (g_i(t,\theta;\Phi) - \tilde{g}_i(t,\theta;\Phi))^2 dt d\theta \qquad (1)$$

where $\Phi$ is a vector of the model parameters, $g_i$ represents the object view data and $\tilde{g}_i$ represents the model view data. That is, the configuration of the model may be optimized by solving for the vector $\Phi$ that minimizes E (i.e., by finding the least squares distance).

Applicant has appreciated that when the structure being modeled is complex and includes a number of deformable parameters, the combinatorial problem of configuring the model may become intractable. That is, as the number of parameters over which the model is allowed to vary increases, the number of possible configurations of the model tends to explode. In addition, Applicant has appreciated that with no guidance on how to initially configure the model, a poorly chosen initial hypothesis may cause a subsequent optimization scheme to converge to an undesirable local minimum. As a result, the selected model configuration may poorly reflect the actual structure that was scanned.

SUMMARY OF THE INVENTION

One embodiment according to the present invention includes a method for determining a value for at least one parameter of a configuration of a model, the model associated with structure of which view data has been obtained, the method comprising acts of detecting at least one feature in the view data, and determining the value for the at least one parameter of the configuration of the model based, at least in part, on the at least one feature.

Another embodiment according to the present invention includes a method of detecting at least one blood vessel from object view data obtained from a scan of the at least one blood vessel, the method comprising acts of generating a model of the at least one blood vessel, the model having a plurality of parameters describing a model configuration, determining a hypothesis for the model configuration based, at least in part, on at least one feature detected in the object view data, and updating the model configuration according to a comparison with the object view data to arrive at a final model configuration, so that the final model configuration represents the at least one blood vessel.

Another embodiment according to the present invention includes a method of iteratively configuring a model adapted to describe at least some internal structure of an object from which object view data has been obtained, the model including a plurality of model components. The method comprises acts of determining a configuration of at least one first model component based, at least in part, on at least one feature detected in the object view data, the at least one first model component representing at least one first substructure in the internal structure, removing information in the object view data corresponding to the at least one first substructure as represented by the at least one first model component, and determining a configuration of at least one second model component based, at least in part, on at least one feature detected in the object view data after the act of removing information.

Another embodiment according to the present invention includes a method of processing view data of structure obtained from an X-ray scanning device capable of scanning, in situ, at least a portion of a human's anatomy, the method comprising an act of detecting at least one dimension of a structure, wherein the at least one dimension is less than 500 microns.

Another embodiment according to the present invention includes a method of processing view data of structure obtained from a micro-computer tomographic (microCT) X-ray scanning device, the method comprising an act detecting at least one dimension of a structure, wherein the at least one dimension is less than 50 microns.

Another embodiment according to the present invention includes a method of processing view data of structure obtained from an X-ray scanning system capable of resolving information to a first minimum size and having an image reconstruction algorithm that generates reconstructed image data from the view data capable of resolving information to a second minimum size, the method comprising an act of detecting a presence of at least some of the structure having a dimension less than the second minimum size.

Another embodiment according to the present invention includes a computer readable medium encoded with a program for execution on at least one processor, the program, when executed on the at least one processor, performing a method of determining a value for at least one parameter of a configuration of a model, the model associated with structure of which view data has been obtained, the method comprising acts of detecting at least one feature in the view data, and determining the value for the at least one parameter of the configuration of the model based, at least in part, on the at least one feature.

Another embodiment according to the present invention includes an apparatus adapted to determine a value for at least one parameter of a configuration of a model, the model associated with structure of which view data has been obtained, the apparatus comprising at least one input adapted to receive the view data, and at least one controller, coupled to the at least one input, the at least one controller adapted to detect at least one feature in the view data and to determine the value for the at least one parameter of the configuration of the model based, at least in part, on the at least feature.

DETAILED DESCRIPTION

Figure 1:
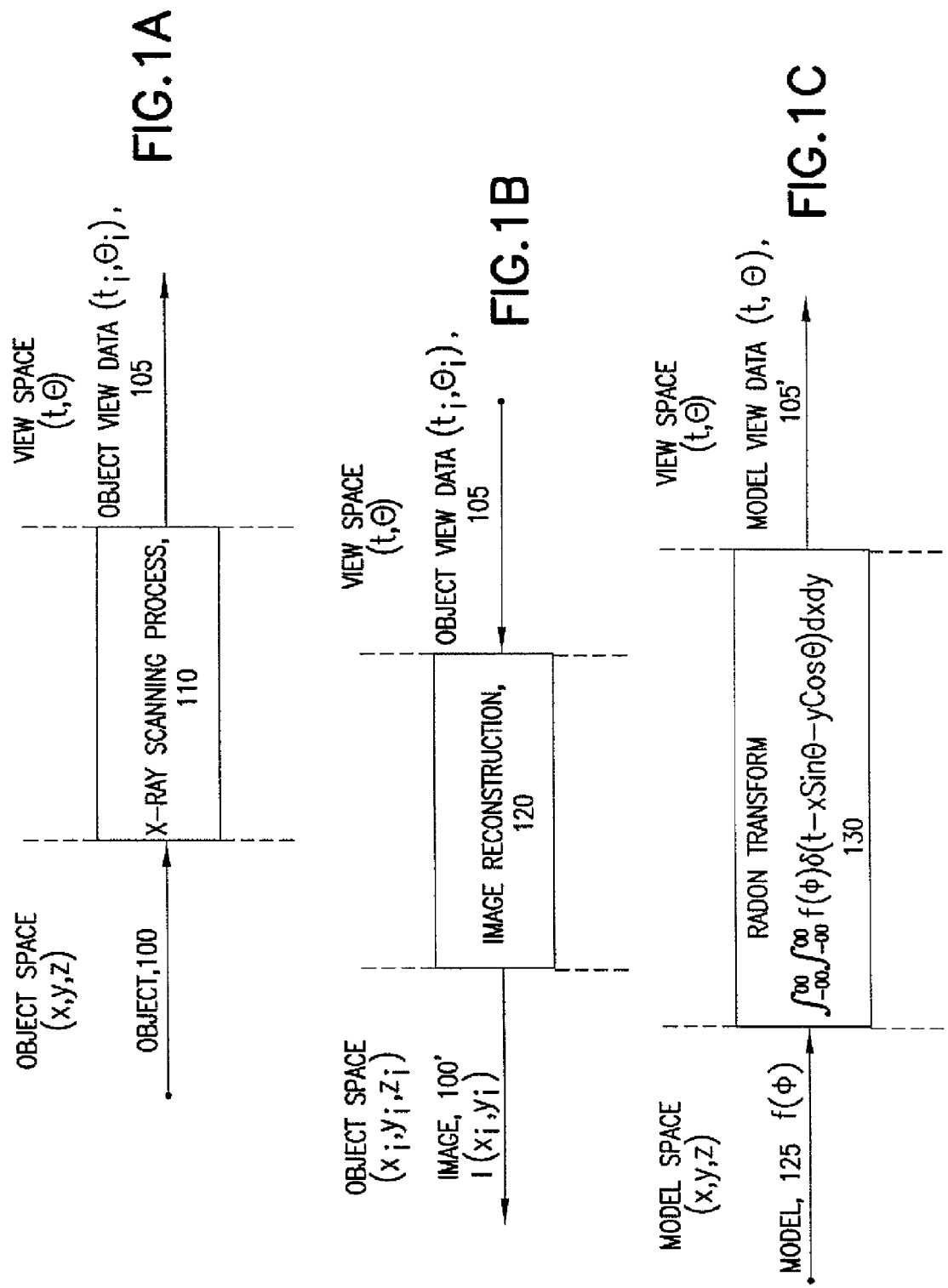
FIGS. 1A, 1B and 1C illustrate transformations of an X-ray scanning process, a image reconstruction process, and the radon transform, respectively.

As discussed above, segmentation of reconstructed images is often difficult and is limited to information describing structure at the reduced resolution resulting from the image reconstruction process. Structure at or below this resolution, though present in the view data, may be unavailable to detection and segmentation algorithms that operate on reconstructed image data. Conventional model based techniques that seek to avoid image reconstruction have been frustrated by the combinatorial complexity of fitting a model configuration to the observed view data.

In one embodiment according to the present invention, a model is generated to describe structure to be detected in view data obtained from scanning the structure. The view data may be processed to detect one or more features in the view data characteristic of the modeled structure and employed to determine a value of one or more parameters of a configuration of the model, i.e., information in the view data may be used to bootstrap a hypothesis about how the model may be configured. By obtaining information about the model configuration from the view data, the combinatorial complexity of fitting the model configuration to observed view data and the likelihood of converging to an undesirable local minimum may be reduced. In addition, by processing the view data directly, structure may be detected at the resolution of the view data (i.e., substantially at the resolving capability of the X-ray scanning equipment.)

In another embodiment according to the present invention, one or more components of a model may be configured based on information in view data obtained from scanning an object of interest. For example, the one or more components may correspond to relatively large structure having the most salient information in the view data. The information in the view data corresponding to the one or more components may then be removed to refine the view data. One or more additional components of the model may be configured based on information in the refined view data. For example, the one or more additional components may correspond to smaller structure having information that was obscured by the more salient information previously removed. By iteratively removing information from the view data, relatively small structures that were undetectable in the first iteration may be detected.

In another embodiment according to the present invention, structure below 500 microns is detected in view data obtained from a conventional large object X-ray scanning device, more preferably below 250 microns, more preferably below 100 microns, and even more preferably below 50 microns.

In another embodiment according to the present invention, structure at or below 50 microns is detected in view data obtained from a microCT scanning device, more preferably below 25 microns, more preferably below 10 microns, and even more preferably below 5 microns.

One application for the model-based detection techniques described herein relates to use with the pulmonary vessel network of humans, which is a relatively complex structure, wherein blood vessels with relatively large radii may branch off into blood vessels with smaller radii and so on. The ability to detect and segment this structure may provide a foundation for detection and/or characterization of many forms of disease of the lungs and heart such as the family of conditions known as chronic obstructive pulmonary disease (COPD), which includes: emphysema; lung cancer; pulmonary emboli; idiopathic pulmonary fibrosis; and pulmonary arterial hypertension.

In one embodiment, a model of a vessel network may be generated having a plurality of parameters that describe a model configuration. The configuration may include defining values for any one of or combination of the position, orientation, scale, etc., of each component or primitive of the model. Features detected in view data obtained from, for example, X-ray scanning a portion of the pulmonary vessel network, may be employed to form a hypothesis regarding the configuration of the model. The configuration may then be optimized to obtain a resulting model configuration that provides a best fit to the view data. The resulting model configuration describes the portion of the vessel network and may be used to characterize the vessel network, for example, to make a clinical assessment related to the onset or extent of COPD.

Following below are more detailed descriptions of various concepts related to, and embodiments of, methods and apparatus according to the present invention. It should be appreciated that various aspects of the inventions described herein may be implemented in any of numerous ways. Examples of specific implementations are provided herein for illustrative purposes only. For example, while many of the embodiments are described in connection with view data obtained using X-ray technology, the aspects of the invention described herein are not limited to use with X-ray technology and may be used with view data from other sources, including but not limited to positron emission tomography (PET) scanners, single positron emission computed tomography (SPECT) scanners, and magnetic resonance imaging (MRI) devices.

Figure 2:
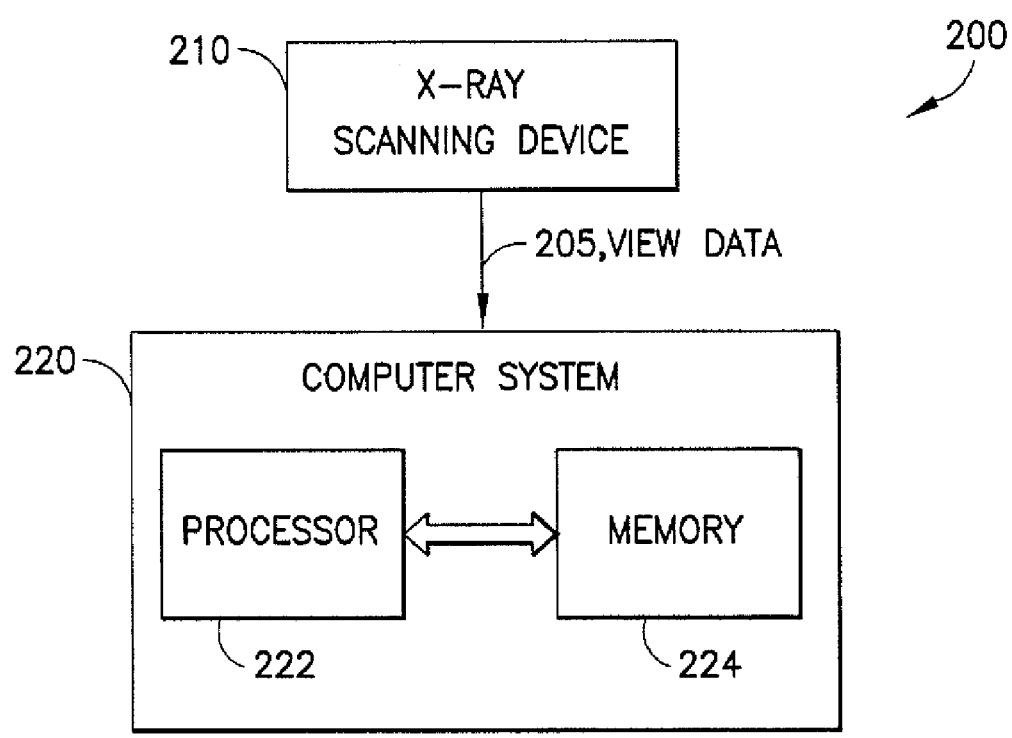
FIG. 2 illustrates one example of a system including an X-ray scanning device and a computer system suitable for practicing various aspects of the invention.

FIG. 2 illustrates a block diagram of one embodiment of a system 200 suitable for practicing various aspects of the present invention. System 200 includes an X-ray scanning device 210 and computer system 220. X-ray scanning device 210 may be any device capable of acquiring view data of an object of interest. X-ray scanning devices may be designed with varying capabilities, such as resolution, scan speed and scan path (e.g., circular, helical, etc.), may employ a variety of radiation emission technologies, such as cone beam, fan beam and pencil beam technologies, and may be arranged in numerous configurations, such as circular or rectangular geometry detector arrays, and may provide data of different types such as CT or laminographic data. Any X-ray scanning device providing view data may be suitable, as aspects of the invention are not limited to view data obtained from any particular type, arrangement and/or capability. As discussed above, view data may be obtained from other types of scanning devices, as aspects of the invention are not limited for use with view data obtained from X-ray scanning devices.

Computer system 220 may include a processor 222 connected to one or more memory devices including memory 224. Memory 224 may be any of various computer-readable media capable of storing electronic information and may be implemented in any number of ways. Memory 224 may be encoded with instructions, for example, as part of one or more programs that, as a result of being executed by processor 220, instruct the computer to perform one or more of the methods or functions described herein, and/or various embodiments, variations and combinations thereof.

Computer system 220 may be, for example, a personal computer (PC), work station, general purpose computer, or any other computing device. Computer system 220 may be integrated into X-ray scanning device 210 or may be a separate stand alone system, either proximate to or remote from X-ray scanning device 210. For example, computer system 220 may be connected to X-ray scanning device 210 over a network, connected to multiple scanning devices or may not be connected to any X-ray scanning device at all. In this last respect, computer system 220 may operate on view data previously stored in memory 224, or may obtain the view data from some other location, e.g., another computer system, over a network, via transportable storage medium, etc. It should be appreciated that any computing environment may be used, as the aspects of the invention described herein are not limited to use with a computer system of any particular type or implementation.

Figure 3:
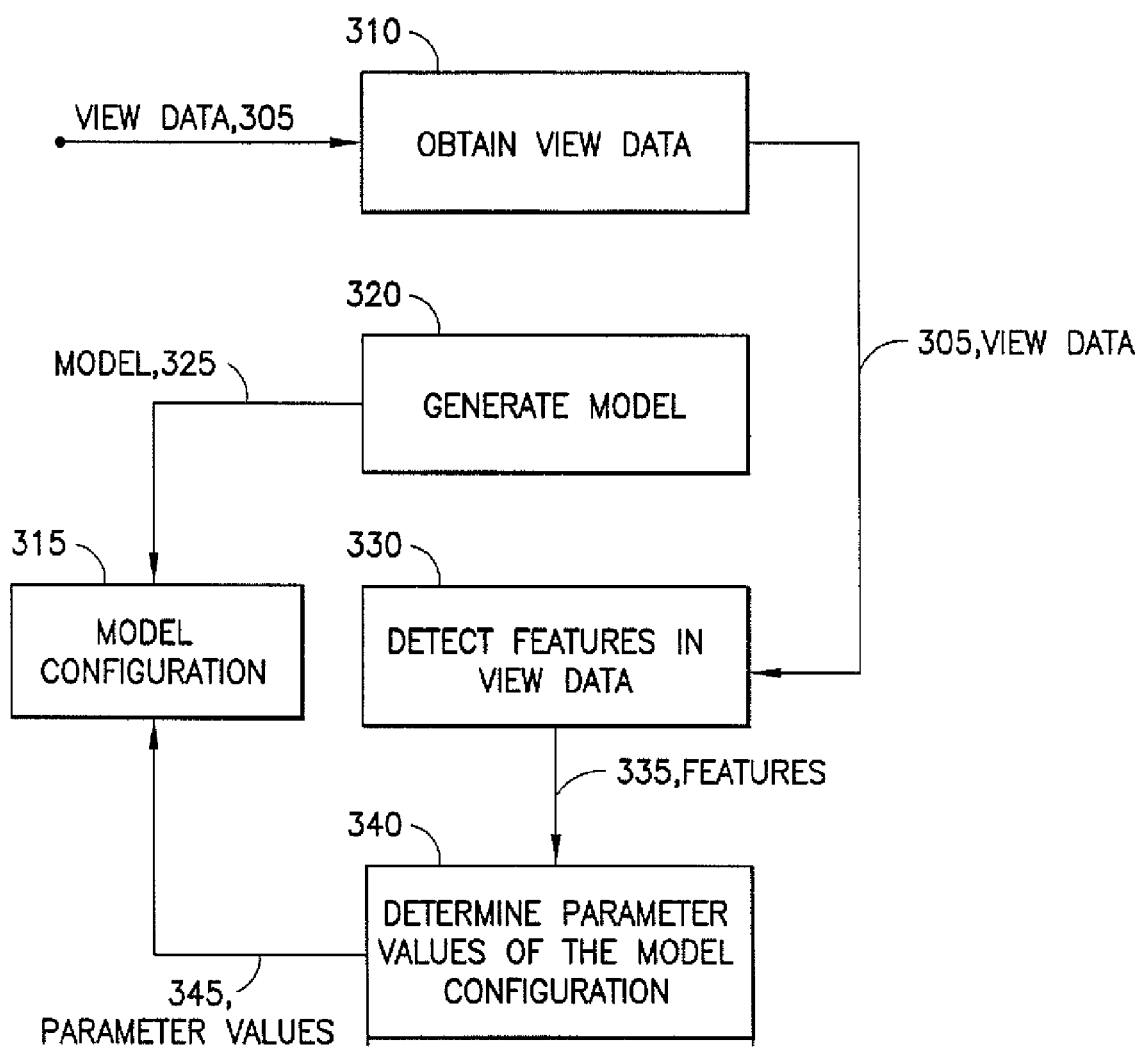
FIG. 3 illustrates a method of determining a value for at least one parameter of a model configuration from features detected in view data in accordance with one embodiment of the present invention.

FIG. 3 illustrates a method according to one embodiment of the present invention for determining a configuration of a model based on information detected in view data of an object of interest. In act 310, view data 305 of an object of interest is obtained. The view data may correspond to a 2D slice of the object of interest or may correspond to 3D information formed from scanning a plurality of two-dimensional slices of the object of interest. View data 305 may be obtained in any suitable way, as the invention is not limited in this respect. For example, the view data may be obtained directly from an X-ray scanning device, from a storage medium storing previously obtained view data, over a network, etc.

In act 320, a model 325 of at least some of an object's structure is generated, the model 325 including one or parameters that define a configuration 315 of the model. For example, the model may include parameters that describe the location and/or orientation in space of the model's component parts, may include a density distribution of the model, etc. Initially, the model may be unconfigured, i.e., the model parameters may not have assigned values. Accordingly, model configuration 315 may be expressed in variable form. For example, the model may be stored as one or more classes or data structures in a memory (e.g., memory 224 in FIG. 2) having various class methods or functions capable of initializing the parameters to configure the model once one or more of the parameter values have been determined.

The choice of the model and the mathematical description may depend on the type of structure being described. For example, a triangulated surface or other deformable mesh may be used to describe various shapes such as biological and/or anatomical structures. Open or closed parameterized curves (e.g., snakes) may be used to define the boundaries or otherwise segment a variety of structures of interest. A model may also be formed from geometric primitives such as ellipses or cylinders to build a description of a particular structure, for example, portions of the human vasculature. A primitive refers to any base component from which a model is built. Any of various parameterized or deformable models may be used, as aspects of the invention are not limited for use with any particular type of model.

In act 330, some information concerning view data 305 is processed to detect one or more features in the view data that may indicate how the model should be configured. A feature may be any property, characteristic or pattern detectable in view data. For example, a feature may be any information characteristic of the modeled structure that indicates that the modeled structure was present to some extent during a scan that produced the view data and/or indicates one or more properties of the structure such as its location, orientation, scale, etc. A feature may include one or more detectable properties that facilitate the detection of the feature by any of various image processing techniques. In one embodiment, a feature may be detected by identifying particular relationships between multiple pixel intensities in the image that are characteristic of the structure being modeled. For example, detecting a feature may include, but is not limited to, identifying a characteristic greyscale pattern, locating one or more derivative properties such as detectable edge characteristics, or locating one or more other higher order derivative properties such as ridges.

The type of characteristic features to be detected may depend on the type of structure being identified, detected and/or segmented in the X-ray data. Knowledge of how a particular structure projects into view space may indicate the type of features to expect in the view data when such structure is present during the scan. In this respect, the radon transform of a model 325 may be employed to gain an understanding of what view data of the model looks like and what features can be expected to arise in the view data when X-ray views of the structure are obtained.

In act 340, the one or more detected features characteristic or indicative of structure of interest are used to facilitate a hypothesis for a configuration of model 325. For example, the detected features may be used to determine one or more parameter values 345 to be assigned to model configuration 315. Once a hypothesis has been established, the configuration of the model may be optimized so that it best describes the observed view data 205. The optimized model configuration may then be employed to characterize the modeled structure. For example, the optimized configuration may be used to form an image of the modeled structure, for example, by sampling the geometry to form a 2D or 3D image of the modeled structure. In addition, the resulting geometry may be assessed or otherwise analyzed to provide information about the modeled structure. This information may be provided to an operator, such as a physician, to aid in diagnosing a medical condition or an anatomical anomaly.

As discussed above, conventional model based techniques are vulnerable to combinatorial explosion due in part to a lack of information regarding how the model should be configured to best describe the arrangement of the modeled structure that was scanned, since the presence, amount and configuration of the structure is generally a priori unknown. By using information in the view data to constrain the model, optimization of the configuration may become a less complex operation and less susceptible to converging to an undesirable local minimum.

Figure 5A:
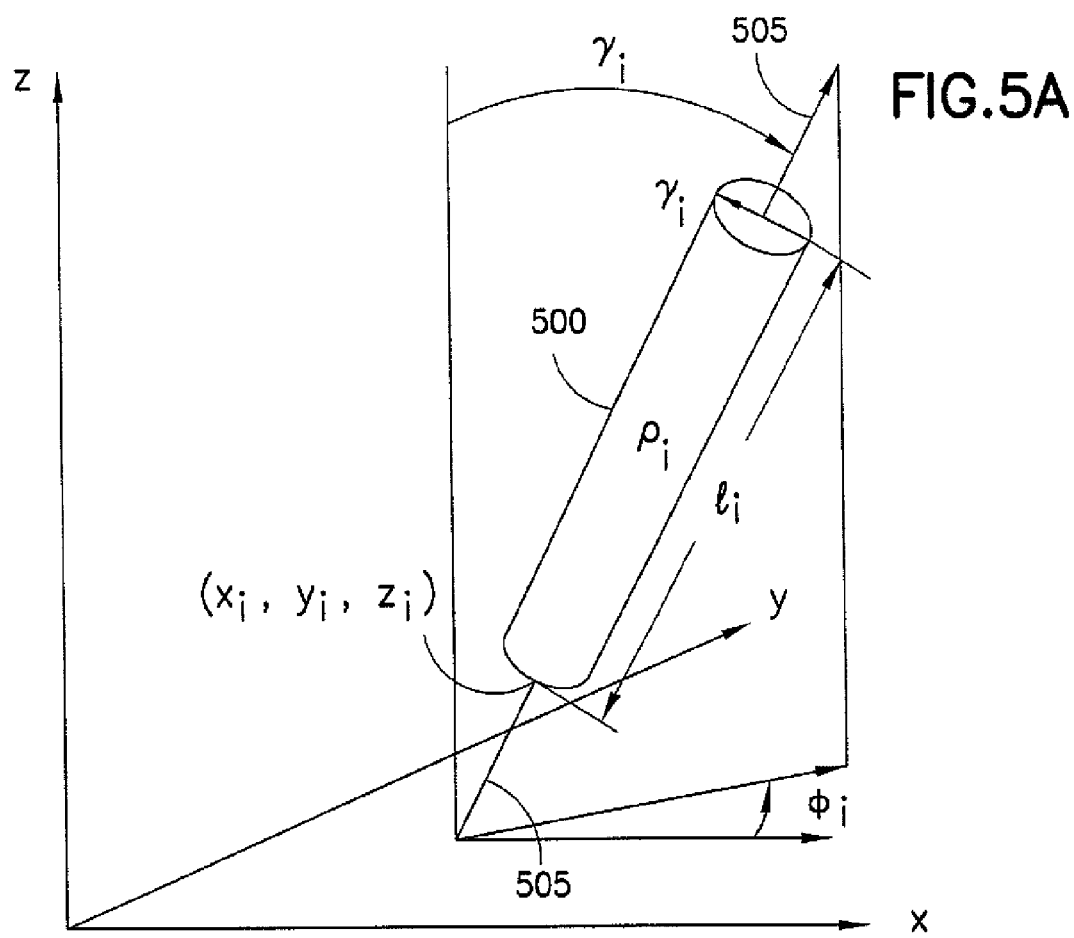
FIG. 5A illustrates a cylinder model in accordance with one embodiment of the present invention.

FIG. 5A illustrates one example of a cylindrical segment 500 that may be used as a component primitive in a cylinder network model. A configuration of cylindrical segment 500 may be described by a number of parameters in a particular coordinate frame (i.e., parameterized in model space). As discussed above, model space may be the same 3D coordinate frame as an object or structure being modeled (i.e., model space and object space may describe the same space). For example, the position of cylindrical segment 500 may be described by a location of the cylindrical axis 505 at a point $(x_i, y_i, z_i)$ in space, for example, the origin or termination of the cylindrical segment. The orientation of cylindrical segment 500 may be specified by the angle $\emptyset_i$ from the x-axis and the angle $\gamma_i$ from the y-axis. Since cylindrical segment 500 is axially symmetric, its rotation about the z-axis may not need to be specified. The length of the cylindrical segment may be specified by $l_i$ and the radius of the cylindrical segment 500 may be specified by $r_i$. Accordingly, cylindrical segment 500 may be configured by assigning values to the seven parameters $x_i$, $y_i$, $z_i$, $\emptyset_i$, $\gamma_i$, $l_i$ and $r_i$.

Figure 5B:
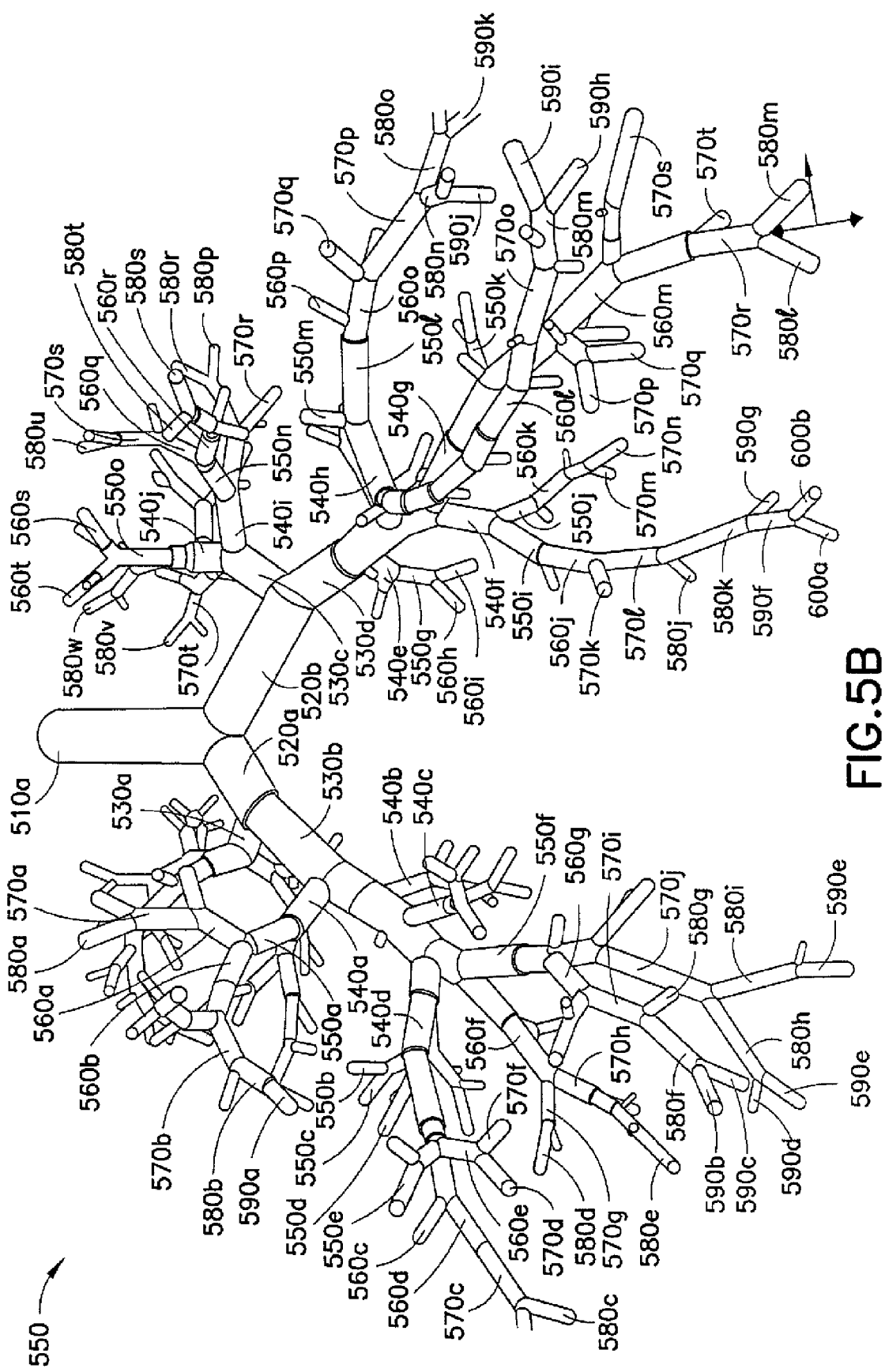
FIG. 5B illustrates a configuration of a cylinder network model built from the cylinder model in FIG. 5A, in accordance with one embodiment of the present invention.

FIG. 5B illustrates a configuration 550 of a cylindrical network model formed from a plurality of cylindrical segments arranged in a hierarchy. As discussed above, a vessel structure may include numerous vessels, each vessel having its own configuration in space to be described by the model. Configuration 550 includes a cylindrical segment 510a which branches into two cylindrical segments 520a and 520b, which further branch until the network terminates at the leaves of the hierarchy (i.e., cylindrical segments 520 branch into cylindrical segments 530, which in turn branch into segments 540, 550, 560 and so on). Although the specific parameter values are not shown, it should be appreciated that forming configuration 550 involves specifying values for the parameters of each of its component cylindrical segments. Modifying values of one or more of the parameters (including the number of cylindrical primitives in the hierarchy) results in a different model configuration.

It should be appreciated that the exemplary configuration 550 is a simplification of expected configurations for X-ray data with respect to the number of primitives in the configuration. In configuration 550 in example of FIG. 5B, configuration of the model involves specifying 7n parameters, where n is the number of cylindrical primitives. When all the parameters are unknown, optimization of configuration 550 involves several hundred degrees of freedom. A scanned portion of a vessel network may contain many times more vessels than described in configuration 550 (e.g., hundreds or thousands of vessels), making optimization of the configuration increasingly complex.

Arbitrarily choosing a configuration to seed the optimization is likely to result in a configuration that poorly reflects the structure being modeled and may cause the optimization to converge to a distant and undesirable local minimum. As the number of primitives in the model increases to hundreds or thousands or more, the problem may become intractable, especially considering that the number of primitives may also be unknown. In accordance with one embodiment, the view data is used to guide the hypothesis and/or constrain one or more of the model parameters, thus reducing the complexity of optimizing the configuration.

Figure 4A:
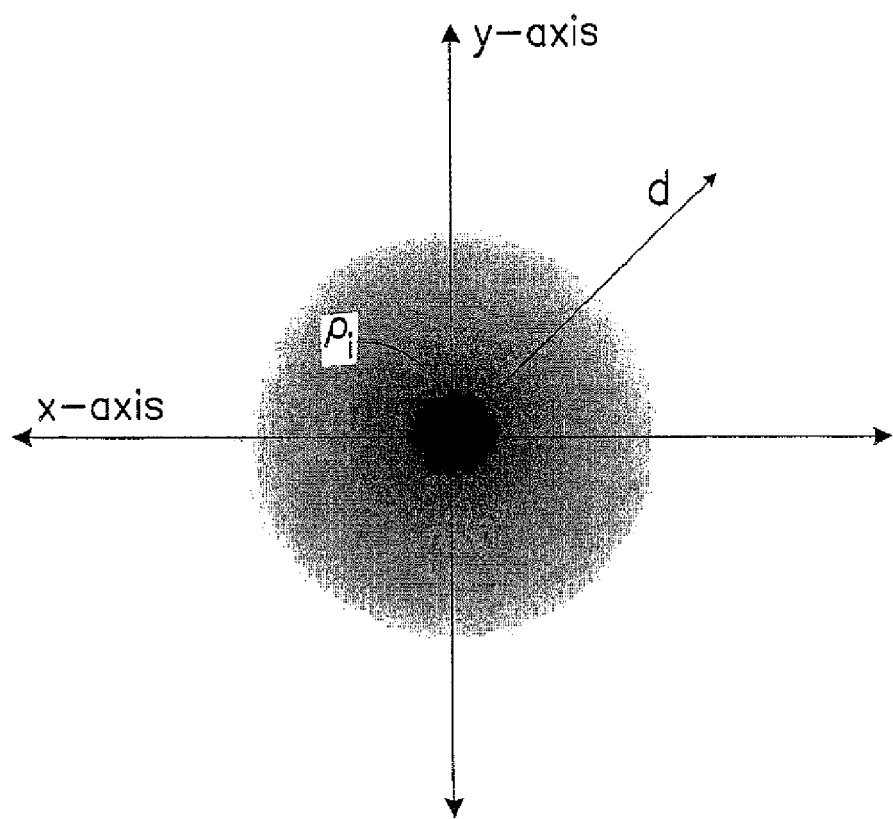
FIGS. 4A and 4B illustrate a greyscale representation and a cross-section of a Gaussian density distribution for use in a model, in accordance with one embodiment of the present invention.
Figure 4B:
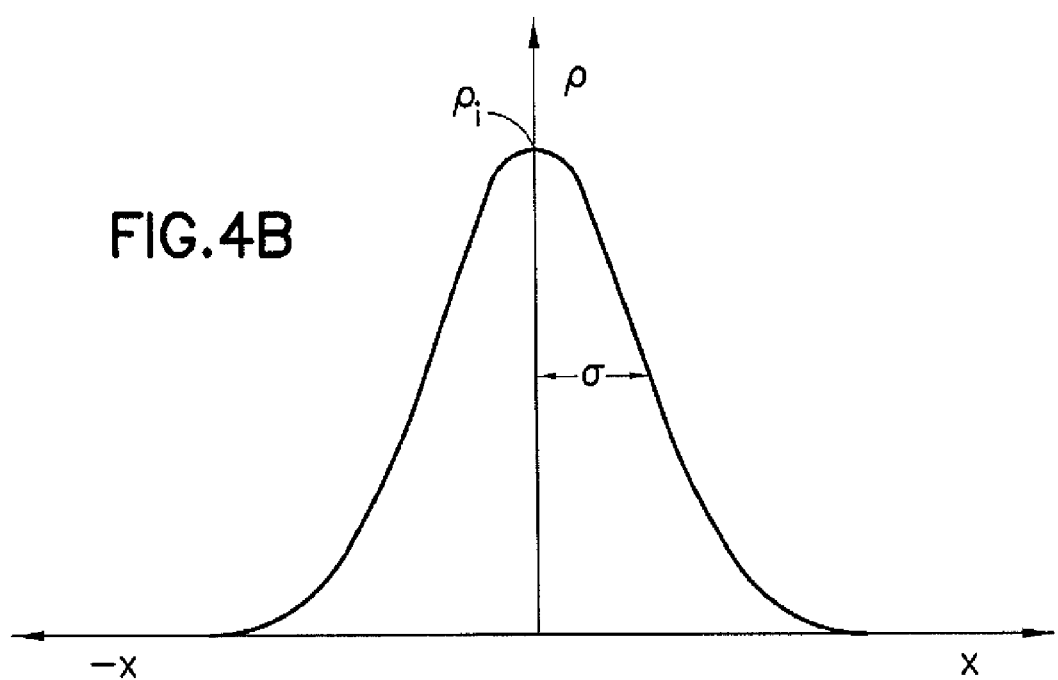

In one embodiment, the density distribution of the structure may also be modeled to understand how the structure projects into view space so that information gleaned therefrom can be used to assist in detecting features in view data corresponding to the modeled structure. For example, blood vessels may exhibit a characteristic density distribution that, when scanned, produces characteristic features or patterns in the view data. In one embodiment, the cross-sectional density of a vessel is modeled by a Gaussian distribution, centered on the longitudinal axis of the vessel, so that the modeled density is the highest at the center of the vessel. For example, the cross-sectional density distribution of cylindrical segment 500, when oriented such that its longitudinal axis coincides with the z-axis, may be modeled as, $$\rho_i e^{-\frac{1}{r_i^2}((x-x_i)^2+(y-y_i)^2)} \qquad (2)$$

where $\rho_i$ is the density coefficient at a center of the $i^{th}$ cylindrical segment and $r_i$ is the radius of the $i^{th}$ cylindrical segment, so that the density is modeled as being greatest at the center of the cylindrical segment (i.e., equal to $\rho_i$) and decays exponentially as a function of radial distance from the center. FIG. 4A illustrates a greyscale representation of the function given in equation 2, where darker greyscale values indicate increased density values. FIG. 4B illustrates a plot of the intensity values along the x-axis at the center of the greyscale Gaussian distribution in FIG. 4A.

The density distribution along the longitudinal axis of the cylinder (i.e., into and out of the page in FIG. 4A) does not vary and may be modeled as a constant function of the cross-sectional distribution along the longitudinal axis, that is, as a constant function of the radial distance d from the center of the distribution. Accordingly, each cylindrical segment in configuration 550 may be assigned the cross-sectional density distribution defined in equation 2.

To express the density distribution at the orientation of a corresponding cylindrical segment, the density distribution may be transformed by the well known coordinate transformation matrix:

$$\begin{pmatrix} \cos[\gamma]\cos[\phi] & -\sin[\phi] & -\cos[\phi]\sin[\gamma] \\ \cos[\gamma]\sin[\phi] & \cos[\phi] & -\sin[\gamma]\sin[\phi] \\ \sin[\gamma] & 0 & \cos[\gamma] \end{pmatrix} \qquad (3)$$

where the angles $\gamma$ and $\phi$ are the orientation parameters defined in FIG. 5A. It should be appreciated that the illustrative modeled density distribution of equation 2 depends only on the model parameters discussed in connection with FIG. 5A. Accordingly, if values have been assigned to each of the model parameters, the distribution may be fully described, such that the density distribution does not introduce any additional parameters. It should be appreciated that the invention is not limited in this respect, as the density distribution may be modeled such that it includes one or more independent model parameters.

The cylinder model described above illustrates one example of a model suitable for describing vessel structures. However, other types of models may be used, as aspects of the invention are not limited in this respect.

Figure 6:
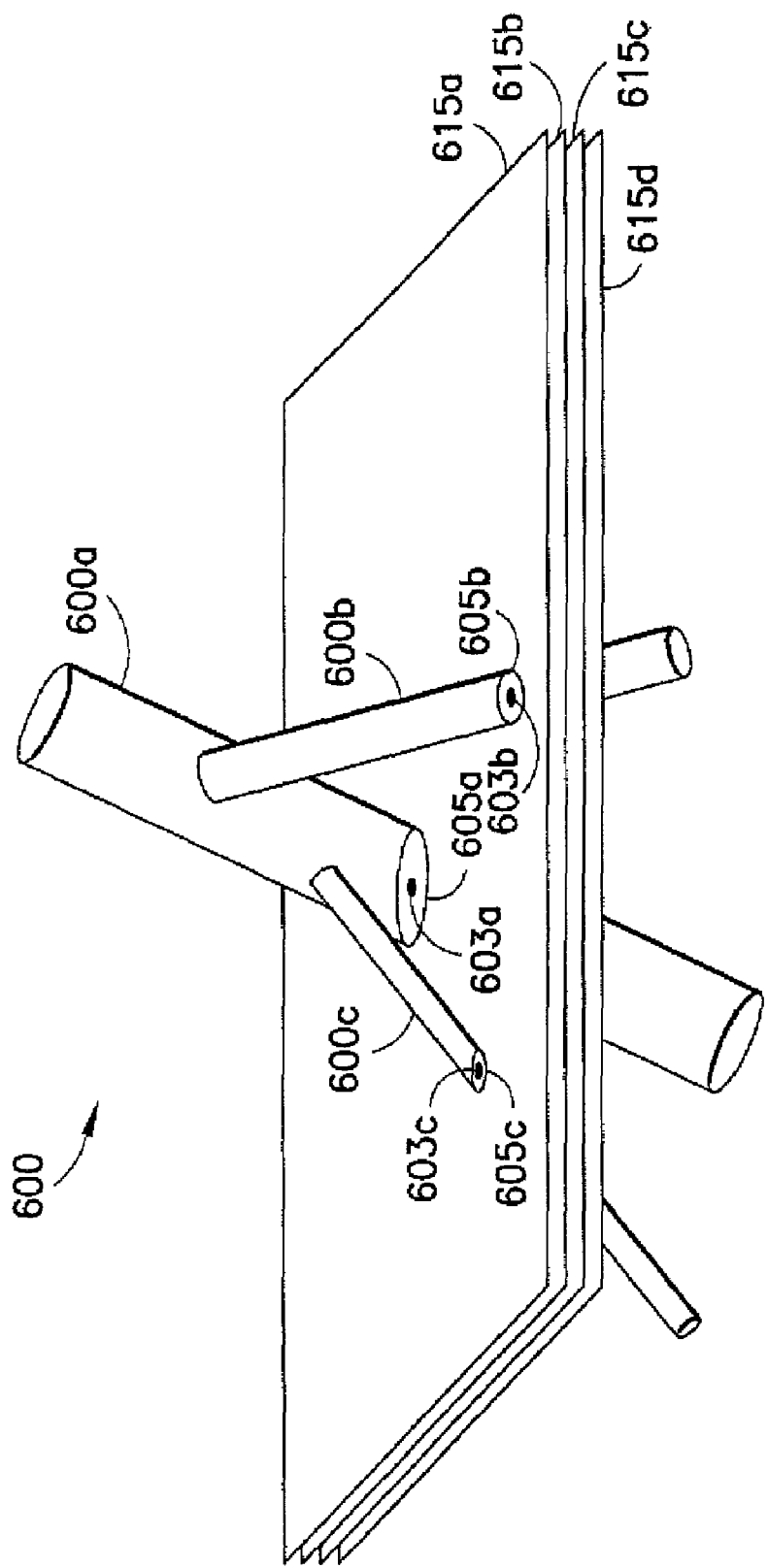
FIG. 6 illustrates characteristic elliptical cross-sections of cylindrical structure as it penetrates a number of scan planes.

As discussed above, view data of a 3D object may be obtained by scanning a plurality of 2D cross-sections of the object. Applicant has recognized that detection of 3D structures of the object may be facilitated by considering how the structure appears when viewed at cross-sectional planes. For example, object 600 in FIG. 6 schematically represents a portion of a vessel network including vessels 600a, 600b and 600c. When object 600 is scanned, a plurality of cross-sectional slices of the object are exposed to X-ray radiation to provide view data corresponding to successive planes intersecting the object, e.g., exemplary planes 615a-615d.

The intersection of plane 615a with each of the cylindrical vessel segments produces respective ellipses 605a-605c, each having an eccentricity that depends on the angle the respective vessel segment cuts with the plane. Therefore, the presence of a 3D vessel segment may be detected by exploiting the recognition that from the perspective of an X-ray scanner, the vessel segments may appear as a succession of ellipses each having a characteristic density distribution (e.g., the density distribution described in equation 2).

It should be appreciated that when detecting features in 2D slices, the parameter $z_1$ in FIG. 5A may be implied by the corresponding slice and therefore may not need to be determined to configure a cylindrical segment. In addition, in a scan plane, dimensions along the z-axis are infinitesimal. The appearance of the cylindrical segment in the plane is independent of the segment's length, so that the parameter $l_i$ may go unspecified. Accordingly, in a 2D slice, a cross-section of a cylinder segment may be configured by assigning values to five parameters (i.e., $x_i$, $y_i$, $\phi_i$, $\gamma_i$, and $r_i$).

Figure 9:
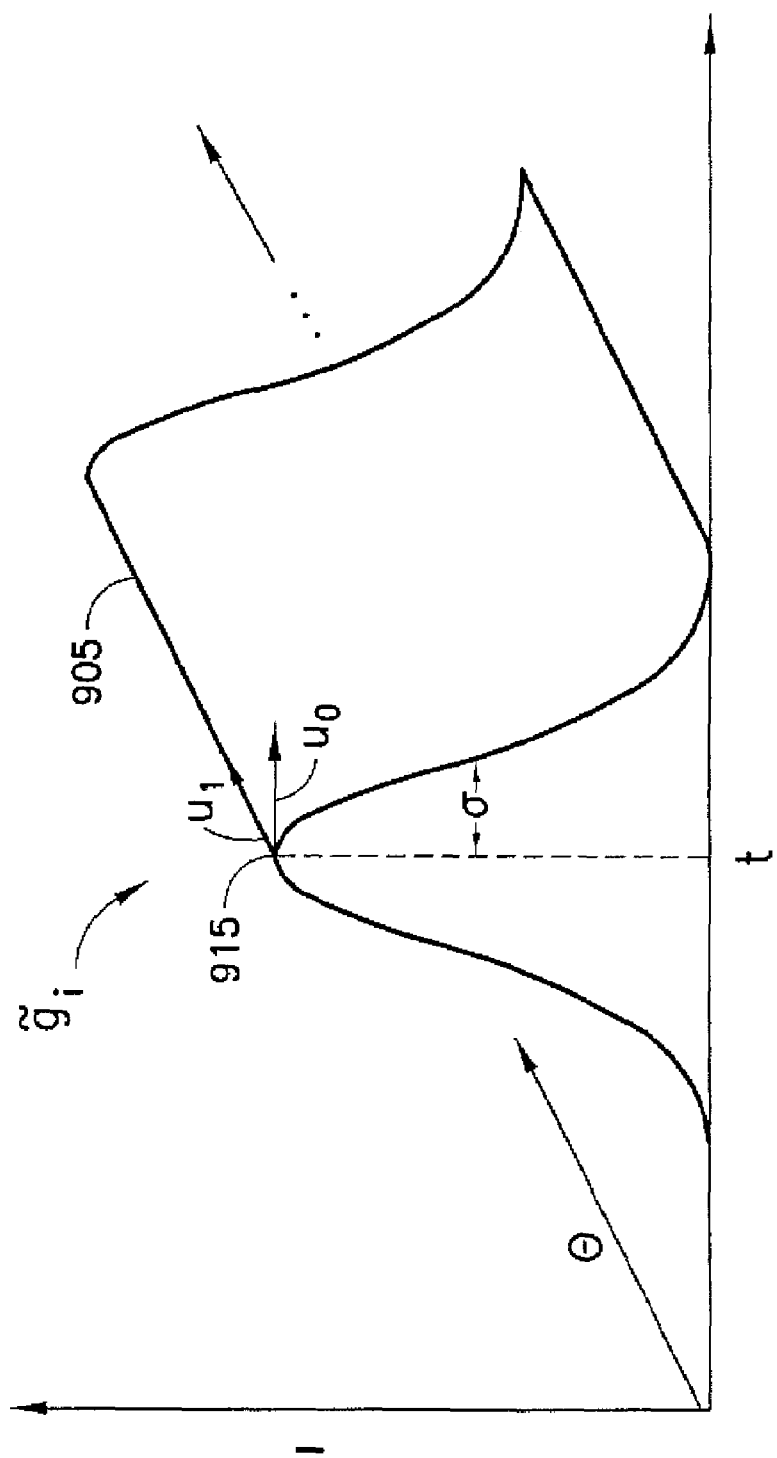
FIG. 9 illustrates a plot of a segment of a sinusoidal trace having a Gaussian profile resulting from taking the radon transform of a Gaussian density distribution.

To identify characteristic features in view data obtained from scanning vessel structures, a cross-section of a cylindrical primitive (i.e., an ellipse) having the density profile described in equation 2 may be projected into view space, e.g., by taking the radon transform of the density profile as discussed above. Accordingly, applying the density distribution in equation 2 to the general formulation of the radon transform gives, $$\tilde{g}_i(t, \theta; \Phi) = \int_{-\infty}^{\infty} \int_{-\infty}^{\infty} \rho_i e^{-\frac{1}{r_i^2}((x-x_i)^2 + (y-y_i)^2)} \delta(t - x\mathrm{Sin}\theta - y\mathrm{Cos}\theta) dx\, dy \quad (4)$$

which results in the expression, $$\tilde{g}_i(t, \theta; \Phi) = \sqrt{\pi}\, \rho_i r_i e^{-\frac{1}{r_i^2}(x_i \mathrm{Sin}\theta + y_i \mathrm{Cos}\theta - t)} \quad (5)$$

where t and θ are axes of the coordinate frame in 2D view space and Φ represents the model parameters. Accordingly, when a blood vessel is scanned, it can be expected to give rise to information in the view data similar to the shape expressed in equation 5, which describes a sinusoidal function having a Gaussian profile. FIG. 9 illustrates schematically a segment of the function $\tilde{g}_i$ expressed in equation 5. Along the t-axis, $\tilde{g}_i$ has a characteristic Gaussian component. Along the θ-axis, $\tilde{g}_i$ has a characteristic sinusoidal component. As θ increases, the Gaussian component (i.e., the Gaussian profile along the t-axis) traces out a sinusoid.

While only a short segment of the sinusoid (a small fraction of the period) is illustrated, it should be appreciated that peak 915 of the Gaussian profile will trace out a sinusoid (better shown in FIG. 8) as indicated by sinusoidal segment 905. As discussed below, this characteristic shape of the transformed Gaussian density distribution can be better understood by examining view data obtained from scanning an elliptical structure. In particular, scanning structure similar to the modeled cylindrical cross-section should produce discrete data that approximates the function of equation 5 due to the similar operations provided by the X-ray scanning process and the radon transform as discussed in connection with FIGS. 1A and 1C.

Figure 7:
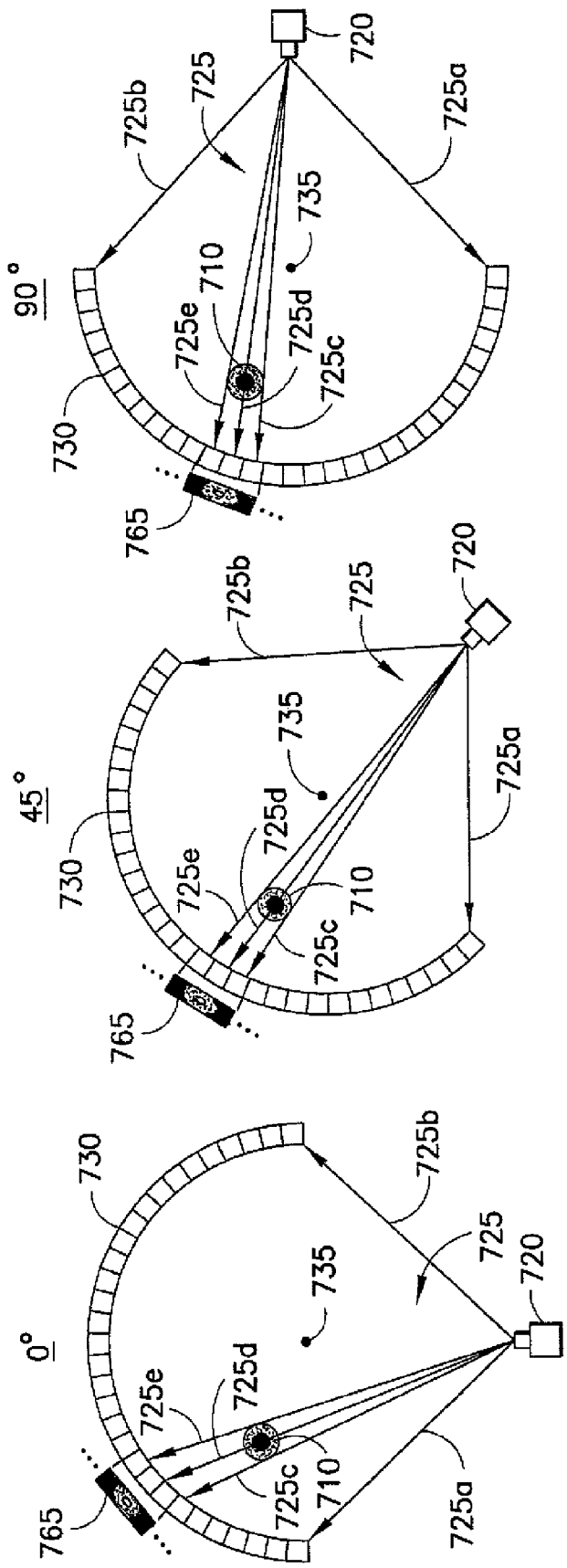
FIG. 7 illustrates an exemplary X-ray scanning process of an elliptical object having a Gaussian density distribution.

FIGS. 7A-7C illustrate a scanning operation of an ellipse 710 having a Gaussian density distribution, such as shown in FIGS. 4A and 4B. For example, ellipse 710 may be a cross-section of a vessel structure having a cross-sectional density similar to the density distribution in equation 2. The view data obtained from the scan is represented by sinogram 800 illustrated schematically in FIG. 8. FIG. 7A illustrates a snapshot of portions of an X-ray scanning device 700 at a 0° orientation, including a radiation source 720 adapted to emit X-ray radiation and an array of detectors 730 responsive to the X-ray radiation. Radiation source 720 may emit a substantially continuous fan beam 725, e.g., over an arc between rays 725a and 725b defining the extent of the fan beam. The radiation source 720 may be positioned along the circular extensions of the semi-circular and detector adapted to rotate together with detector array 730 about a center point 735.

As the radiation source 720 and the detector array 730 rotate about center point 735, the detectors in the array respond to impinging X-rays by generating a detection signal, for example, an electrical signal proportional to the intensity of the radiation impinging on respective detectors. As a result, the detector array records the radiation intensity profile at various orientations of the source and array with respect to ellipse 710. The detection signals generated by each detector in the array may be sampled to obtain values indicating the intensity of an X-ray extending substantially in a line between each detector and the radiation source. The detector array may be sampled, for example, at a degree angle interval, half-degree angle interval, quarter-degree angle interval, etc., as the device rotates to obtain a number of projections of the ellipse at different views. FIGS. 7B and 7C illustrate snapshots of the X-ray scanning device at 45° and 90°, respectively. A 2D scan of ellipse 710 may include obtaining projections of ellipse 710 over a 180° arc at a desired angle interval Δθ.

The majority of the radiation emitted by source 720 will impinge unimpeded on the detector array 730. However, some portion of the rays will pass through ellipse 710 before reaching the detector array. The impeded rays will be attenuated to an extent related to the density of ellipse 710. Exemplary rays 725c and 725e substantially tangent to the object will be the least attenuated rays of those that pass through the ellipse. Rays passing substantially through the center of ellipse 710 (e.g., ray 725d) have the most material to penetrate at the highest density and therefore will exhibit the greatest attenuation.

The detectors in the "shadow" of ellipse 710, therefore, will detect radiation having a profile that transitions from zero attenuation at the tangent of ellipse 710, to a peak attenuation at the center of ellipse 710, and back to zero attenuation at the other tangent of ellipse 710, as shown by profile 765. For example, profile 765 may be a greyscale representation of the detection signals provided by the detectors in the array that are in the shadow of the ellipse, wherein lighter gray levels indicate greater X-ray attenuation. Accordingly, detectors that are not in the shadow of ellipse 710 produce detection signals having substantially black grayscale values. As expected from the Gaussian component of equation 5, i.e., the Gaussian profile illustrated in FIG. 9, profile 765 has a characteristic Gaussian shape. That is, the Gaussian density distribution of ellipse 710 projects Gaussian attenuation information onto the detector array.

Profile 765 is illustrated at a higher resolution than the detector array, i.e., profile 765 includes more than a single greyscale value for each detector in the shadow of ellipse 710 to illustrate the characteristic Gaussian shape of the profile. However, it should be appreciated that each detector illustrated in detector array 730 may be considered as any number of individual detectors generating detection signals such that a profile may be provided at the resolution of the illustrated profile 765.

As the X-ray device rotates, the density distribution of the ellipse will project onto a changing combination of detectors. A 360° rotation of the device causes ellipse 710 to orbit center point 735 (from the perspective of radiation source 720) causing the location of the ellipse projection on the detectors to repeat. As expected from the sinusoidal component of equation 5 (of which a segment is illustrated in FIG. 9) ellipse 710 casts a periodic shadow that falls on the detectors at locations that trace across the detector array as a sinusoid as the orientation of the device increases, which can be mapped to 2D view space as discussed below.

Figure 8:
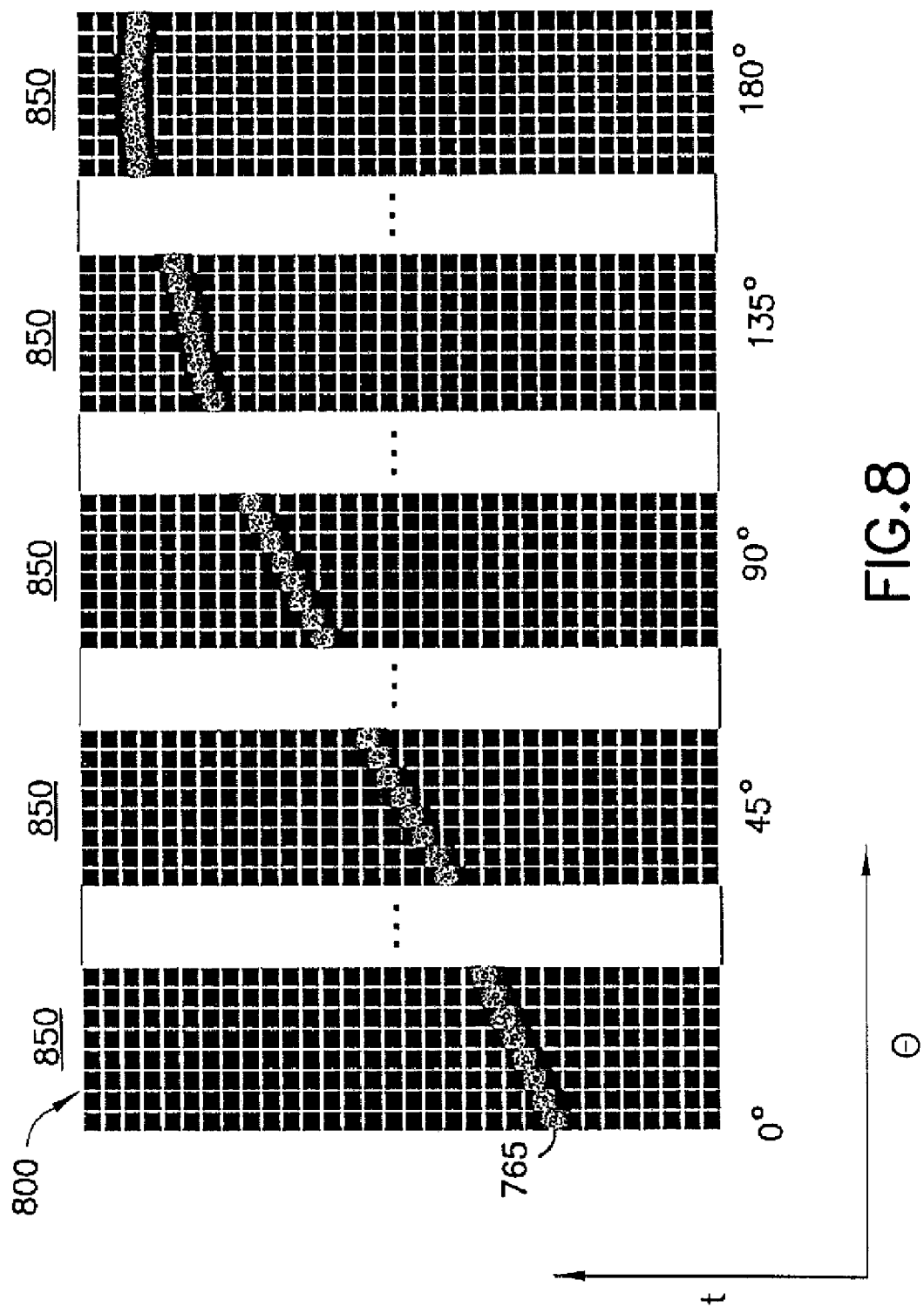
FIG. 8 illustrates a schematic of a sinogram of the view data obtained from the X-ray scanning process illustrated in FIG. 7.

FIG. 8 illustrates a sinogram 800 of the view data obtained from scanning ellipse 710 over a 180° degree rotation at an angle interval of one degree. A sinogram is an image representation in view space of view data. In particular, a sinogram maps intensity values (e.g., attenuation values, density values, etc.) to a discrete coordinate location in view space. Sinogram 800 has axes of θ and t, where θ represents the orientation of the X-ray device with respect to ellipse 710 and t refers to a location along the detector array. Accordingly, sinogram 800 provides a greyscale image of the detections signals generated by detector array 730 as the X-ray scanning device rotates.

Specifically, sinogram 800 includes a grid of pixels 850, wherein each pixel has an intensity related to a sample of a detection signal from a respective detector in array 730 at a particular orientation of the X-ray device. For example, the first column of pixels (θ=0), indicates samples from respective detectors responding to impinging radiation at a 0° orientation of the X-ray device. As a result, the characteristic profile 765 from the detectors in the shadow of ellipse 710, centered approximately at the ninth detector in the snapshot illustrated in FIG. 7A, appears centered approximately at pixel (0,9) in the sinogram. The second column of pixels indicates samples from respective detectors responding to impinging radiation at a 1° orientation of the X-ray device and so on at degree angle intervals.

As θ increases, the location of the profile 765 traces out a portion of a sinusoid that reaches its half-period substantially at a 180° orientation. Portions of the sinogram 800 are illustrated in the vicinity of a 45° orientation, a 90° orientation, a 135° orientation and a 180° orientation to illustrate the sinusoidal transition of the location of profile 765 during the scan. It should be appreciated that the sinusoidal trace visible in sinogram 800 provides a discrete approximation (represented as a greyscale image) of the function expressed in equation 5 (and illustrated in FIG. 9). Therefore, according to the model, a vessel structure that penetrates a particular scan plane or slice will generate a sinusoidal trace having a Gaussian profile in the sinogram associated with the slice. Detecting the presence of such characteristic sinusoids in the sinogram may indicate that the associated structure (e.g., a cross-section of a vessel) was present when the structure was scanned.

Figure 10:
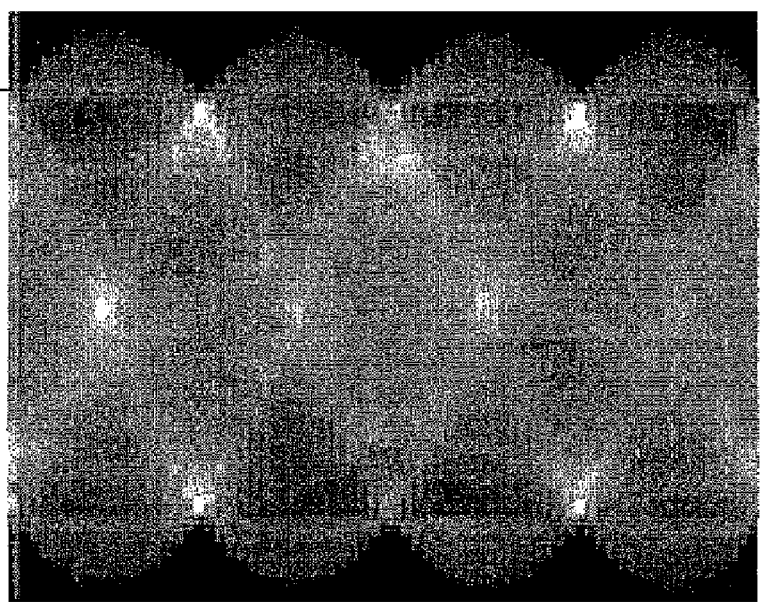
FIG. 10 illustrates an exemplary sinogram of view data obtained from scanning unknown structure.

View data obtained from a scan of an object is likely to include sinusoidal traces from a variety of different structures (as opposed to the single trace in sinogram 800). Projection information associated with the different structures may superimpose in view space. FIG. 10 illustrates a sinogram obtained from scanning an object having multiple unknown structures. Sinogram 1000 results from the superposition of numerous sinusoidal traces, some which may correspond to structure of interest and some which may not. To detect the structures of interest, features characteristic of the structure of interest may be distinguished from information corresponding to other structure and detected in the sinogram.

A Gaussian intensity distribution (e.g., the profile resulting from structure having a Gaussian density distribution) forms a ridge at the peak of the distribution. For example, peak 905 in FIG. 9 forms a ridge that follows along the sinusoidal trace. Similarly, the lightest pixels in each of the Gaussian profiles 765 (i.e., corresponding to the most attenuated X-rays) form a ridge point. Accordingly, ridge detection may be performed to identify characteristic features arising from a cross-section of the modeled vessel structure by locating ridge points in a sinogram formed from view data obtained from vessel structures.

A ridge point may be defined as a point in an image wherein the intensity assumes a local extrema in the direction of principal curvature, i.e., the direction having the steepest intensity gradient. For example, at point 915 (and along peak 905) in FIG. 9, the principal direction of curvature is shown by $u_0$ (i.e., the unit vector (1,0) in the (t, θ) coordinate frame). Each point along peak 905 forms a ridge point since each point is a local maximum along the t-axis (i.e., along the Gaussian profile). The term ridge is used herein to describe both local minimum and local maximum (i.e., to describe both crests and troughs having the above defined ridge characteristics).

A ridge may be characterized by local derivative information in the sinogram and may be detected by examining the curvature of intensity about points of interest in the sinogram. In one embodiment, a Hessian operator is used to extract curvature information from the sinogram to faciliate the detection of ridge points. In general terms, the purpose of applying the Hessian operator is to gather information concerning the way in which the intensity values vary in the pixels surrounding a pixel of interest. As discussed below, this information may be used to identify areas characteristic of a ridge. The Hessian operator in 2D may be expressed as, $$H = \begin{bmatrix} \frac{\partial^2 g}{\partial t^2} & \frac{\partial^2 g}{\partial t \partial \theta} \\ \frac{\partial^2 g}{\partial t \partial \theta} & \frac{\partial^2 g}{\partial \theta^2} \end{bmatrix} \tag{6}$$

where g is the sinogram operated on by the Hessian, and t and θ are the coordinate axes of the sinogram. For example, the Hessian operator may be applied to a sinogram by computing the Hessian matrix at each pixel or each of a subset of pixels in the sinogram, referred to as target pixels. The partial derivative elements of the Hessian matrix may be computed at each target pixel in a variety of ways. For example, the Hessian matrix may be determined by computing appropriate differences in a pixel neighborhood of the target pixel (e.g., an eight pixel adjacency neighborhood of the target pixel). Using a 3×3 neighborhood the Hessian matrix elements may be computed by weighting the pixel intensities according to corresponding elements of a discrete derivative mask and then summing the result. Exemplary derivative masks for the partial derivative elements of the Hessian are:

$$\frac{\partial^2 g}{\partial t^2} = \frac{1}{3}\begin{bmatrix} 1 & -2 & 1 \\ 1 & -2 & 1 \\ 1 & -2 & 1 \end{bmatrix}, \frac{\partial^2 g}{\partial \theta^2} = \frac{1}{3}\begin{bmatrix} 1 & 1 & 1 \\ -2 & -2 & -2 \\ 1 & 1 & 1 \end{bmatrix}, \tag{7}$$

$$\text{and } \frac{\partial^2 g}{\partial t \partial \theta} = \frac{1}{4}\begin{bmatrix} 1 & 0 & -1 \\ 0 & 0 & 0 \\ -1 & 0 & 1 \end{bmatrix}.$$

The center of each matrix corresponds to the target pixel and the intensity of each of the eight adjacent pixels to the target pixel are multiplied by the corresponding element of the mask and summed together. The sum from each mask determines the corresponding element in the Hessian. It should be appreciated that other sized neighborhoods and different interpolating functions (i.e., the mask weights) for the pixels within the neighborhoods may be used, as the aspects of the invention relating to computing discrete partial derivatives are not limited to any particular method or implementation.

As discussed above, the Hessian describes the local curvature of intensity at pixels in the sinogram. The principal direction of curvature may be determined by decomposing the Hessian into its characteristic components. One method of determining the characteristic components of a matrix is to determine the eigenvalues and associated eigenvectors of the matrix.

In general terms, the eigenvectors of the Hessian matrix indicate the characteristic directions of curvature at a target pixel at which the Hessian was determined. As discussed below, the relationship between these characteristic directions of curvature may be employed to identify areas in the sinogram having characteristics of a ridge. The eigenvalues and associated eigenvectors of a matrix may be determined in various ways, for example, by any number of well known iterative methods of diagonalizing a matrix or analytically by directly solving the relationship:

$$Hu = \lambda u \quad (8)$$

where H is the Hessian matrix of equation 6, u is an eigenvector of matrix H, and $\lambda$ is an eigenvalue associated with u. The magnitude of each eigenvalue of the Hessian is related to the "significance" of the associated eigenvector. Stated differently, the eigenvalue indicates how much the curvature along the associated eigenvector contributes to the local curvature determined by the Hessian. Accordingly, the largest eigenvalue of the Hessian matrix is associated with the principal direction of curvature.

As is well known, the 2D Hessian is a 2×2 symmetric matrix and therefore has two eigenvalues, $\lambda_0$ and $\lambda_1$, associated with respective and linearly independent eigenvectors $u_0$ and $u_1$ (i.e., eigenvectors $u_0$ and $u_1$ are orthogonal). The eigenvalue $\lambda_0$ herein denotes the eigenvalue having the greatest absolute value and is referred to as the principal eigenvalue. Accordingly, the associated eigenvector $u_0$ indicates the principal direction of curvature at a target pixel and $\lambda_0$ is related to the magnitude of the curvature. The eigenvalue $\lambda_1$ (referred to as the secondary eigenvalue) is related to the magnitude of curvature in the direction of $u_1$, i.e., in a direction orthogonal to the principal direction of curvature indicated by $u_0$.

At a ridge of a Gaussian profile of a sinusoidal trace, the curvature in a direction along the profile may be expected to be relatively large, while the curvature in an orthogonal direction along the ridge may be expected to be relatively small. Therefore, a ridge point may produce a large principal eigenvalue and a small secondary eigenvalue. For example, expected eigenvectors $u_0$ and $u_1$ are labeled at ridge point 915 in FIG. 9. Since the curvature in the direction of $u_0$ is large, the magnitude of $\lambda_0$ is expected to be large as well. Likewise, since the intensity distribution is expected to be substantially uniform along the sinusoidal trace, the curvature in the direction of $u_1$ is theoretically zero and the magnitude of $\lambda_1$ is expected to be substantially zero. The values of and relationship between $\lambda_0$ and $\lambda_1$ may be employed to determine whether each target pixel at which the Hessian is computed is characteristic of a ridge point. That is, ridge points may have local curvature features expressed by the values of and/or the relationship between $\lambda_0$ and $\lambda_1$ that may be detected by evaluating the eigenvalues.

In one embodiment, a target pixel may be identified as a possible ridge point based on a predetermined criteria for the eigenvalues of the Hessian at the target pixel. For example, a threshold value may be applied to the magnitude of $\lambda_0$ to select as possible ridge points only target pixels having a principal eigenvalue that exceeds the threshold value. In addition or alternatively, a ratio of the magnitude of $\lambda_0$ to the magnitude of $\lambda_1$ may be subject to a threshold value such that ratios exceeding the threshold value are considered to have come from ridge points in the sinogram.

The sign of $\lambda_0$ may also be used to exclude ridges characterized by the wrong extrema (i.e., local minimum versus local maximum). For example, when the grey level scheme of the sinogram represents higher ray attenuation by lighter pixels (higher grey level values) as in FIG. 8, points giving rising to a negative $\lambda_0$ may be ignored (i.e., they indicate troughs rather than crests). Similarly, when the grey level scheme represents higher ray attenuation by lower grey level values, points giving rising to positive $\lambda_0$ may be ignored. Other criteria for evaluating eigenvalues and/or eigenvectors may be used, as aspects of the invention are not limited in this respect.

Accordingly, ridge detection may be applied to a sinogram to select ridge points by evaluating the local curvature characteristics about target points in the sinogram. It should be appreciated that the above technique for locating ridge points is described merely as an example. Any other method suitable for discriminating ridge points from non-ridge points may be used, as aspects of the invention are not limited in this respect. It should be further appreciated that any feature characteristic of structure of interest may be detected, as the invention is not limited to ridges or any other particular property or characteristic.

As discussed above, the identified ridge points may indicate the presence of a Gaussian profile characteristic of a cross-section of a cylindrical structure (e.g., a blood vessel cross-section) in the corresponding slice of the object of interest. It should be appreciated that such ridge points derive their location in view space from the center location of the Gaussian density distribution, e.g., the center of a cross-section of a blood vessel. Accordingly, the location of the detected ridge points in a sinogram may be used to hypothesize the location of the center of a cylindrical segment at a cross-section corresponding to a slice from which the sinogram was obtained.

The detected ridge points may be transformed from view space (i.e., the coordinate frame ($\theta$, t) of the sinogram) to model space (i.e., the coordinate frame (x, y, z) of the model) to determine a number of cylindrical primitives to use in the hypothesis and the location of the cylindrical axis of each of the cylindrical primitives. A sinusoidal trace characteristic of a vessel may generate numerous detected ridge points, for example, a sinusoid of ridge points that track substantially along the center of the trace (e.g., each of the lightest pixels in profile 765 along the sinusoidal trace visible in sinogram 800). However, many of the true ridge points of a particular sinusoidal trace may not be detected amongst other information in the sinogram corresponding to structure that occluded or partially occluded the vessel structure during the scan. Furthermore, as is often the case with thresholding techniques (e.g., the thresholds described above) some false positive ridge points may be detected.

Each ridge point that is part of the same sinusoidal trace is associated with the same ellipse center. Stated differently, each ridge point $(\theta_i, t_i)$ in a same sinusoid in view space will transform to the same point $(x_i, y_i)$ in model space. Since each characteristic sinusoidal trace is assumed to be generated by a corresponding vessel cross-section, the ridge point (i.e., the peak of the Gaussian distribution) corresponds to the center of the elliptical cross-section. Accordingly, the location of the cylindrical axis of a cylindrical segment where it intersects the scan plane corresponds to the transformed location of ridge points of the same sinusoidal trace.

The shape of a sinusoidal trace includes information about the location of corresponding structure in object space. For example, if ellipse 710 in FIG. 7A-7C was positioned directly at center point 735, the ellipse would generate a profile that traces a substantially horizontal line in the resulting sinogram (i.e., a sinusoidal trace having a zero amplitude) since the ellipse would cast a shadow on the same detectors independent of the orientation of the device. If the distance of ellipse 710 from the center point 735 were increased, the amplitude of the corresponding sinusoidal trace would also increase. The variation of the location of the profile is related to the distance of the ellipse from the center point 735. Accordingly, the location of structure in object space (and thus model space) may be determined by examining the characteristics of the corresponding sinusoidal trace in view space in a manner discussed below.

An example of determining object space locations from characteristics of a sinusoidal trace in view space will now be discussed, referring to the illustrative schematic sinogram 1100 shown in FIG. 11, which has a number of superimposed sinusoidal traces in view space resulting from unknown structure. Ridge detection may be applied to sinogram 1100 as discussed above to identify a pixel at $(\theta_0, t_0)$ as a ridge point of sinusoidal trace 1110. At the point $(\theta_0, t_0)$, the slope of the sinusoid 1110 is given by $\tau_0$ and describes in part the shape of the sinusoidal trace. It is known from the radon transform that the sinusoidal trace in view space generated by a point $(x_i, y_i)$ in object or model space, satisfies the expression:

$$x_i \sin\theta + y_i \cos\theta - t = 0 \qquad (9).$$

To obtain two simultaneous equations, equation 9 may be differentiated with respect to $\theta$, resulting in the expression:

$$x_i \cos\theta - y_i \sin\theta - \frac{\partial t}{\partial \theta} = 0. \qquad (10)$$

Figure 11:
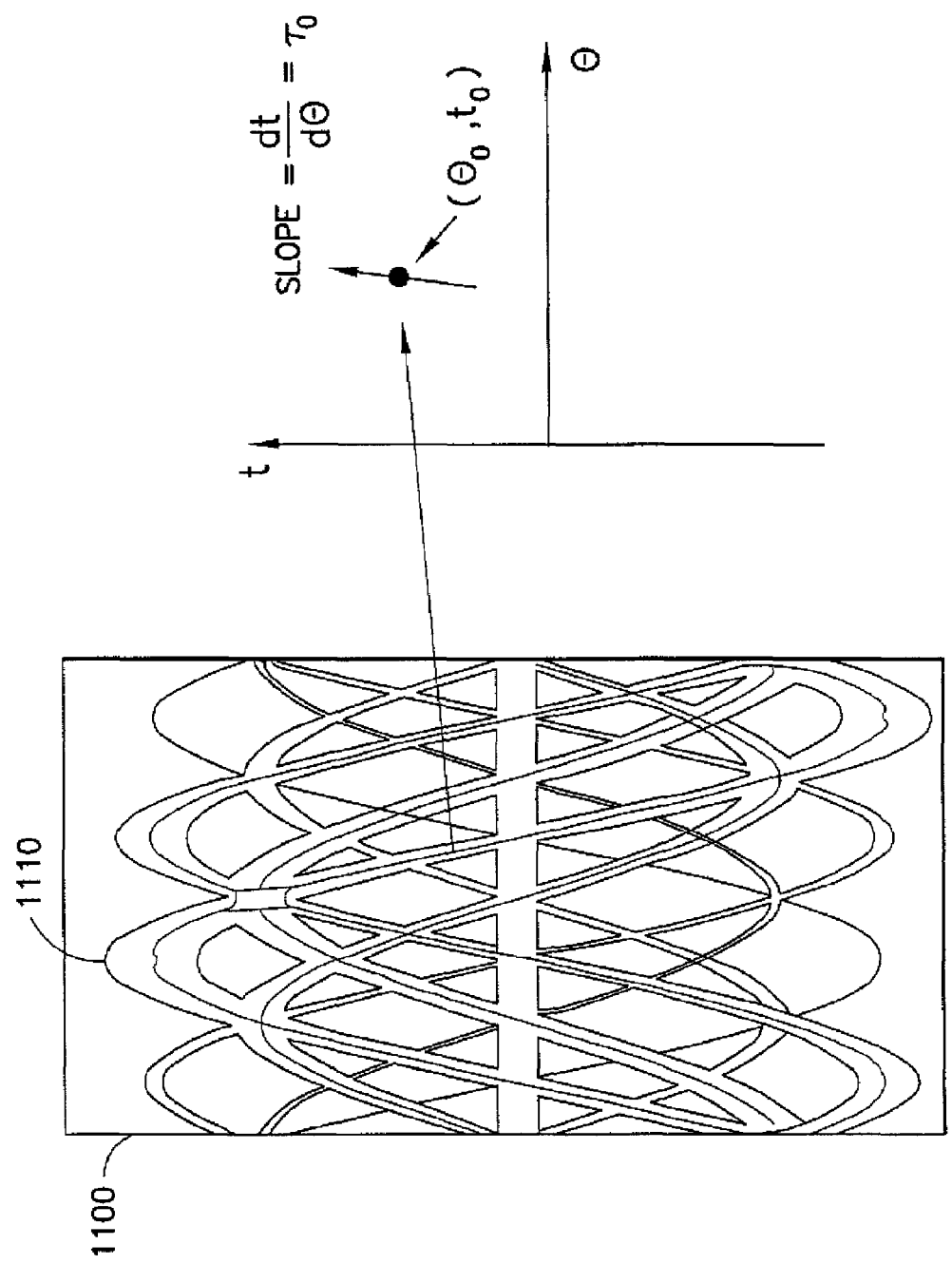
FIG. 11 illustrates a schematic of a sinogram and a slope of a sinusoidal trace at a detected ridge point, in accordance with one embodiment of the present invention.

By using the relationship $$\frac{\partial t}{\partial \theta} = \tau$$

illustrated at $(\theta_0, t_0)$ in FIG. 11, $\tau$ may be substituted into equation 10, resulting in the expression:

$$x_i \cos\theta - y_i \sin\theta - \tau = 0 \qquad (10).$$

Since $\tau$ may be determined as discussed below, equations 9 and 11 provide two equations in two unknowns (i.e., $x_i, y_i$). Solving for the point $(x_i, y_i)$ at the point $(\theta_0, t_0)$ results in the two expressions:

$$x_i = t_0 \sin\theta_0 + \tau_0 \cos\theta_0$$

$$y_i = t_0 \cos\theta_0 - \tau_0 \sin\theta_0 \qquad (12).$$

Accordingly, a point $(\theta_0, t_0)$ in view space may be transformed to a point $(x_i, y_i)$ in object space if the slope of the sinusoidal trace $\tau_0$ at $(\theta_0, t_0)$ is known or can be determined. The slope $\tau$ at a point $(\theta, t)$ may be computed in a variety of ways. For example, the slope $\tau$ may be computed by connecting adjacent detected ridge points to form a ridge segment. However, as discussed above, ridge detection may select a number of false ridge points that may frustrate attempts to connect detected ridge points into the correct ridge segments. Non-maximal suppression may be used to eliminate false ridge points as illustrated in FIGS. 12A-12C.

Figure 12:
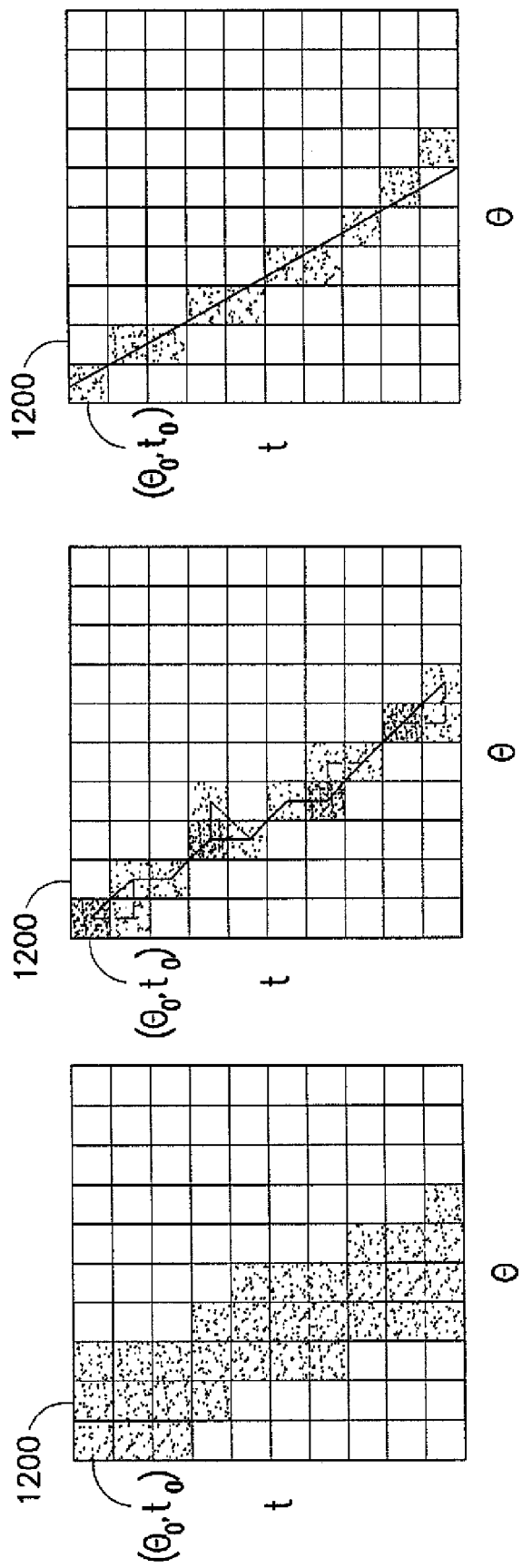
FIGS. 12A-12C illustrates a method of non-maximum suppression for eliminating ridge points identified during ridge detection, in accordance with one embodiment of the present invention.

FIG. 12A illustrates a 10×10 pixel image portion 1200 of a sinogram. For example, image portion 1200 may be a portion of sinogram 1110 in the vicinity of point $(\theta_0, t_0)$. The shaded pixels denote points that were selected as possible ridge points during ridge detection. For example, each of the shaded pixels may have generated a Hessian having eigenvalues meeting some predetermined criteria. As discussed above, a ridge point is a local extrema in the direction of principal curvature. Accordingly, each pixel having an intensity that is not a local maximum may be eliminated. The shaded pixels in FIG. 12B illustrate local maxima computed with respect to the $\theta$-axis.

When two adjacent pixels in the direction of non-maximum suppression have the same local maximum intensity, the pixel that generates the straightest line may be selected. For example, at the darker shaded pixels in FIG. 12B, more than one adjacent pixel could be chosen as belonging to the ridge segment. Pixels that form the straightest path (shown by the solid line segments) are selected over pixels that form the less direct paths (shown by the dotted lines). The shaded pixels in FIG. 12C illustrate the resulting ridge segment in local image portion 1200. The slope of the best fit line connecting the pixels in the ridge segment may be used as $\tau$ at each of the ridge points in the ridge segment (e.g., as $\tau_0$ at ridge point $(\theta_0, t_0)$).

The slope $\tau$ may also be computed individually at each target ridge point by taking the slope of the line connecting the selected ridge points in a local neighborhood of the target ridge point (e.g., estimating the slope by the connecting line through the target ridge point and the previous adjacent and subsequent adjacent ridge point). In detected ridge segments that are long, the local slope may provide a more accurate determination of the true slope of the sinusoidal trace at any given target ridge point. In FIGS. 12A-12C, non-maximal suppression was applied along the $\theta$-axis. However, non-maximal suppression may be applied in any direction (e.g., in the direction of the principal eigenvector of the Hessian computed at the target ridge point). Alternatively, the slope $\tau$ may be determined at each ridge point according to the secondary eigenvector $u_1$. As shown in FIG. 9, eigenvector $u_1$ may point in a direction along the sinusoidal trace and may be used to estimate the slope $\tau$ in the transformation equations above.

The techniques described above are described merely as examples. Any suitable method for transforming points in view space to object space may be used, as the aspects of the invention are not limited in this respect.

As discussed above, each ridge point identified during ridge detection may be transformed to a coordinate location in model space. This transformed location corresponds to a hypothesized center of an elliptical cross-section, which in turn indicates the model space location where the axis of a cylindrical primitive intersects the plane of the associated slice (e.g., locations 603a-603c in FIG. 6). As discussed above, each ridge point belonging to a single sinusoidal trace should transform to the same coordinate location in model space. However, imprecision in computations (e.g., discrete partial derivative computations, tangent and/or slope computations, etc.), may cause particular transformed coordinates to deviate from the true model space location. However, transformed locations from multiple ridge points of the same sinusoidal trace can be expected to concentrate in a generally focused area. A location may be selected from this local concentration in any suitable way. For example, a histogram may be formed of locations transformed from each of the detected ridge points. Each ridge point effectively casts a vote for a location in model space.

In one embodiment, the histogram may be formed by discretizing model space into a grid. Each transformed ridge point may then be appropriately binned into the nearest location in the grid. Information in the resulting histogram may then be employed to determine both the number of cylindrical primitives to be used to configure the model, and the location of each primitive (i.e., the location of the longitudinal axis of the cylindrical primitive at an intersection with the plane of the corresponding slice).

In one embodiment, a cylindrical primitive is added to the cylinder network model for each local maximum or peak in the histogram. The cylindrical axis location of each added primitive may be initialized to correspond to the coordinate position in the grid corresponding to the peak in the histogram. Alternatively, the number and location of cylindrical primitives may be determined by computing the centroid about local maxima in the histogram to determine the location of each cylindrical primitive. Other methods such as statistical approaches may also be employed to parse the histogram to determine the number and location of primitives in a configuration of the model, as the invention is not limited in this respect.

By determining the number of and location (i.e., parameters $x_i$, $y_i$) of cylindrical primitives that intersect a given slice, the combinatorial complexity of optimizing the model is significantly reduced. As discussed above, parameters for a cylindrical segment may include $x_i$, $y_i$, $\varnothing_i$, $\gamma_i$, and $r_i$ for each of the segments in the cylinder network model. The remaining model parameters in the configuration (e.g., $\varnothing_i$, $\gamma_i$ and $r_i$) for each of the determined primitives may be chosen in any suitable manner (e.g., based on a priori knowledge of the structure in the object of interest, by sampling a uniform distribution of values for each parameter, etc.). For example, the radii of the cylindrical primitives may be selected based on knowledge of the vessel size in the object or based on certain vessel sizes of particular interest.

Once the model has been configured, model view data of the model may be generated by taking the radon transform of the configured model. The model view data may then be compared with the object view data (i.e., the view data obtained from the X-ray scanning process) to obtain a measure of how well the configuration describes the structure that gave rise to the object view data. The configuration may then be updated until the model view data satisfactorily describes the object view data. Updating the configuration may be carried out using any suitable optimization technique. The optimized configuration may then be used as a description of the structure of interest in the object that was scanned.

Figure 13:
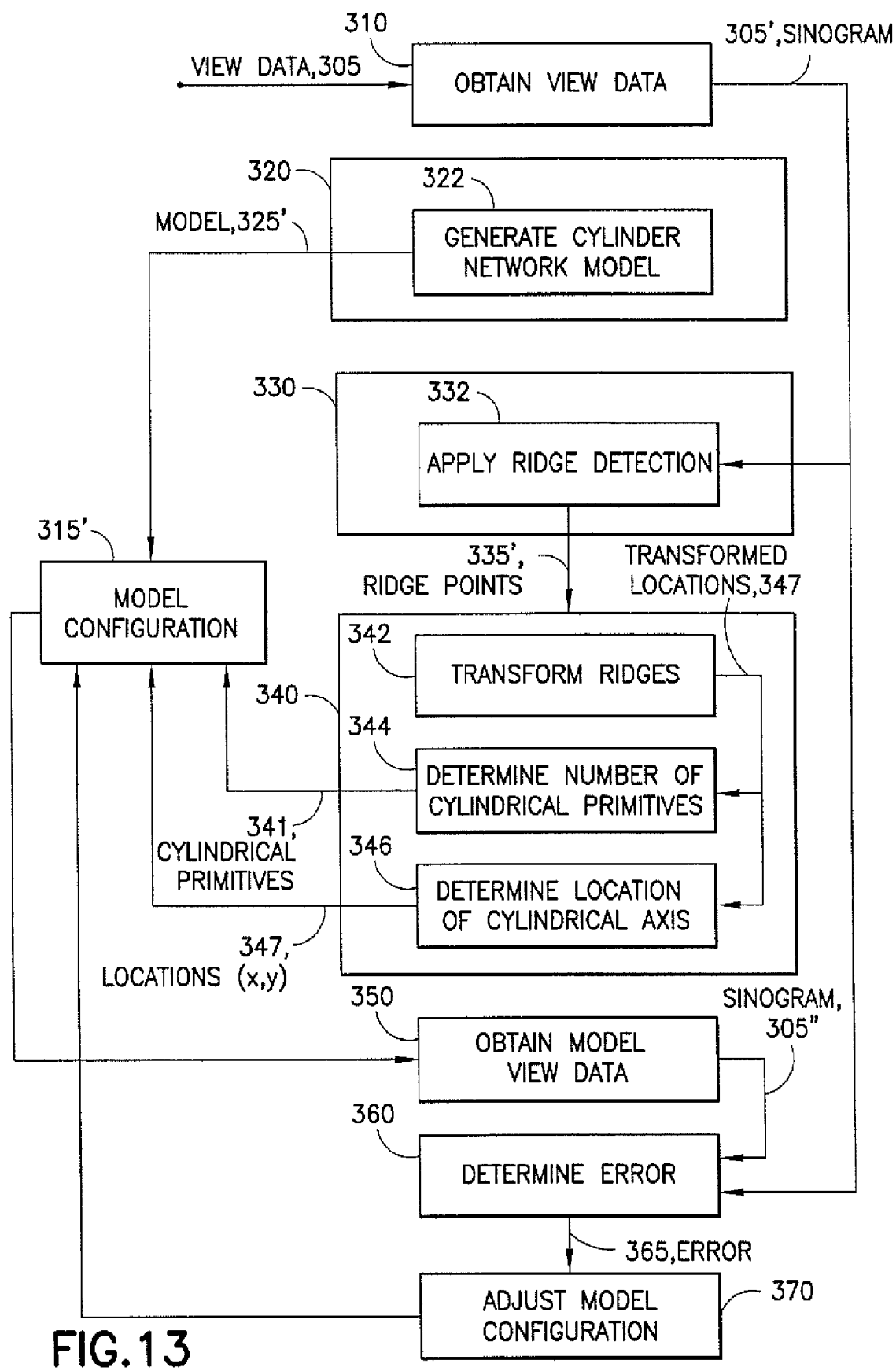
FIG. 13 illustrates a method of determining a number and location of cylindrical segments in a cylinder network model from features in the view data in accordance with one embodiment of the present invention.

FIG. 13 illustrates one embodiment of a more specific implementation of the method described in FIG. 3, particularly for the detection of vessel structures using techniques described above. For example, view data 305 may have been obtained by scanning a human patient (e.g., a patient's lung including a portion of the pulmonary vessel network). In the embodiment illustrated in FIG. 13, view data 305 includes sinogram 305' corresponding to a 2D cross-sectional scan of the vessel network.

In act 322, a model of the vessel structures is generated. In one embodiment, a parameterized cylinder network model 325' (e.g., such as the cylinder network model described in FIGS. 5A and 5B below) is used to model the structure and shape of the vessel network. For example, the vessel network may be modeled by an unknown number of the cylindrical segments described in FIG. 5A, each having a cross-sectional density distribution described in equation 2. Since nothing specific may be known about the vessels that were scanned, cylinder network model 325' is initially not configured, i.e., values have not been assigned to the parameters of the model configuration 315'.

In act 332, ridge detection is applied to sinogram 305' to detect ridge points 335'. As dicussed above, ridge points are features characteristic of the presence of vessel cross-sections and may be used to determine one or more initial values for the parameters of model configuration 315'. Other features, either alone or in combination with ridges, may be detected in the sinogram, as the aspects of the invention related to obtaining information from the view data is not limited to any particular type of feature, property or characteristic. In act 342, the detected ridge points 335' in the coordinate frame of sinogram 305' are transformed into a respective plurality of transformed locations 347 in the coordinate frame of cylinder network model 325'.

In act 344, the number of cylindrical segments in the model 325' is determined from the transformed locations 347. As discussed above, the locations of transformed ridge points indicate the location of the center of the density distribution (i.e., the center of a cylindrical segment) in a plane corresponding to the slice from which sinogram 305' was obtained. To determine the number of cylindrical segments, a histogram of the transformed locations may be formed and a cylindrical segment 341 added to model configuration 315' for each peak in the histogram.

In act 346, the location of the axis of each cylindrical segment in the plane corresponding to sinogram 305' is determined by assigning the locations 347' of the histogram peaks to centers of respective cylindrical cross-sections. The determined locations 347' provide initial values for the location parameters ($x_i$, $y_i$) for each of the cylindrical segments for an initial hypothesis of model configuration 315'. Having established the number and location of the cylindrical segments at a cross-section corresponding to sinogram 305', initial values for the remaining parameters (e.g., radius and orientation) may be selected in any suitable manner to determine the initial hypothesis of model configuration 315'.

In act 350, model view data is obtained, for example, by projecting model configuration 315' (e.g., a cross-section of the model where values to the model parameters have been assigned) into view space via the radon transform. For example, a cross-section corresponding to sinogram 305' of each cylindrical primitive in model configuration 315' may be projected into view space according to equation 5 to form a model sinogram 305".

In act 360, an error value 365 is determined to quantify how well the model configuration describes the structure (e.g., the pulmonary vessel network) that was scanned, by comparing model sinogram 305" with object sinogram 305' to generate a difference measure. For example, an error value 365 may be computed by taking the squared difference between sinograms 305' and 305" similar to the energy formulation in equation 1. In act 370, model configuration 315' may be modified in an effort to reduce the error value. This process (i.e., acts 350-370) may be repeated until the error value has substantially converged.

Acts 350-370 may be carried out using any suitable optimization technique. For example, known techniques such as a gradient descent method or a constrained regression method may be used. Statistical algorithms such as maximum likelihood or expectation maximization (EM) may be used to select a configuration most likely to have given rise to the observed view data. Other optimization techniques may used, as aspects of the invention are not limited in this respect. It should be appreciated that in the embodiment described above, the number and location of each cylindrical primitive has been determined, based at least in part, on information in the view data, so that the configuration is more likely to be initialized in the vicinity of a desirable solution and is less likely to converge to a local minimum that poorly reflects the structure being modeled.

As discussed above, the optimized configuration of the model may be used as a foundation to provide other information about the subject matter that was scanned. In one embodiment, a high resolution image of the modeled structure may be obtained from the configured model by sampling the model at a desired resolution. For example, since each cylinder described in FIG. 5A may be described by a continuous function, it may be sampled as desired to form 2D and 3D images at substantially any resolution. In another embodiment, clinical information is determined from the configuration of the model. For example, information on the shape, number and/or arrangement of components in the model configuration may be used to characterize the modeled structure.

This information may be provided to a physician to aid in the diagnosis and/or treatment of a patient, for example, in the detection and diagnosis of pulmonary emboli.

In one embodiment, optimization of an initial model configuration may be further improved by determining values of one or more of the remaining parameters (e.g., radius and orientation for a cylinder) from observed view data for use in an initial hypothesis of the model configuration. In one embodiment discussed below, greyscale surface characteristics local to detected ridge points are employed to determine the radius of one or more of the cylindrical primitives comprising the cylinder network model.

Figure 14:
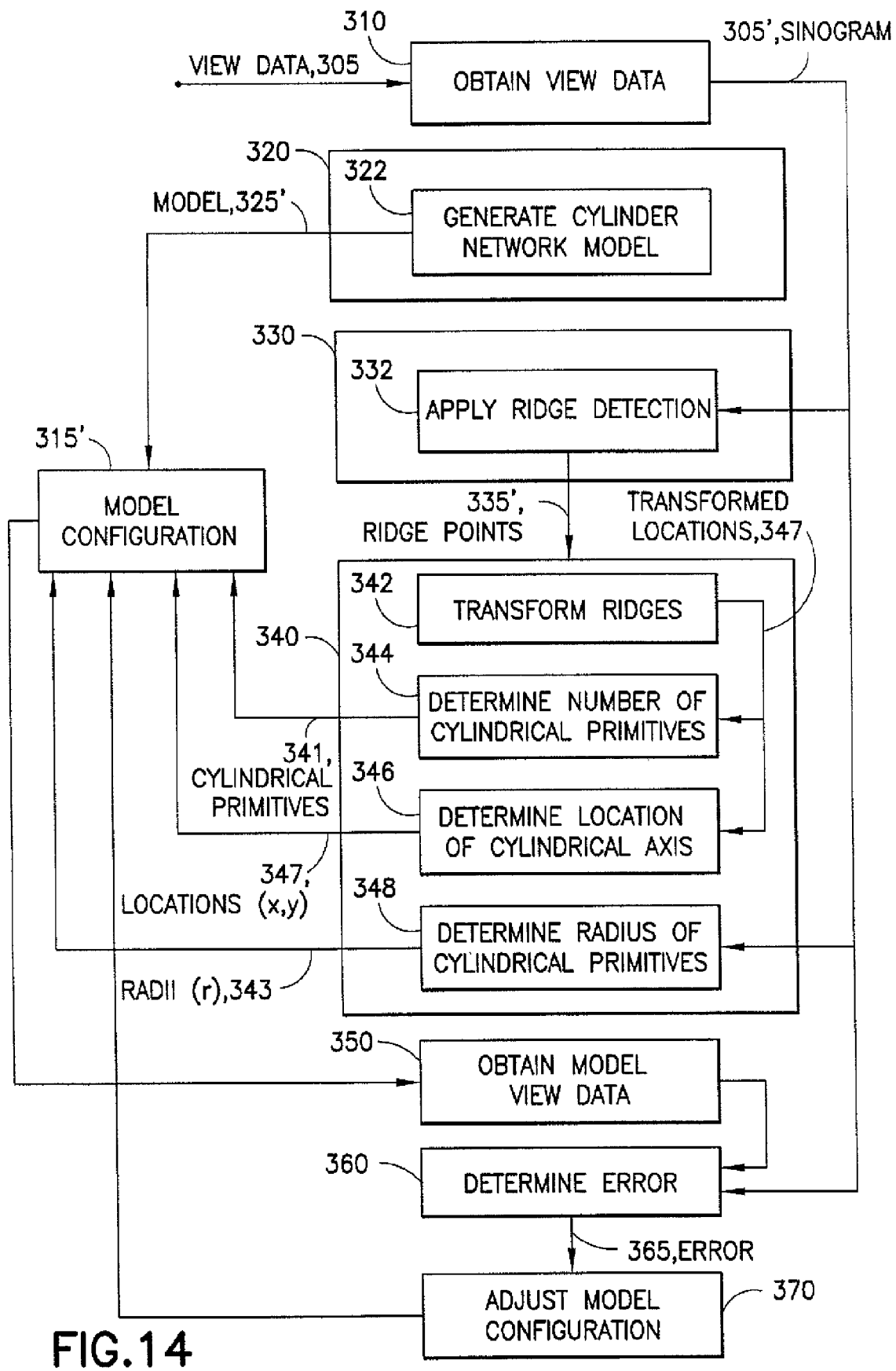
FIG. 14 illustrates a method of determining a number, location and radius of cylindrical segments in a cylinder network model from features in the view data in accordance with one embodiment of the present invention.

FIG. 14 illustrates a method according to one embodiment of the present invention for determining model parameters from the view data. The method illustrated in FIG. 14 is similar in many ways to the method of FIG. 13. However, in an act 348, an initial value for the radius of each cylindrical primitive 341 in the cylinder network model 325' may be determined from information in sinogram 305'. As discussed above, each detected ridge point corresponds to a peak in the Gaussian profile of the associated sinusoidal trace. The greyscale distribution about the ridge may be analyzed to determine the radius of the associated structure. In particular, as a radius of a cylindrical cross-section is increased, so will the standard deviation of the Gaussian density distribution (i.e., the half-width of the Gaussian at the inflection point as shown by a in FIG. 4B). As the variance of the Gaussian density distribution increases, so will the variance of the Gaussian profile component of the projection of the density distribution (i.e., the width of the Gaussian profile in the sinogram). The standard deviation (i.e., the square root of the variance) of the Gaussian may provide an approximation to the radius and may be expressed as, $$r_i^2 = \frac{dg}{dt}\left(\frac{d^2g}{dt^2}\right)^{-1} \quad (13)$$

where g is evaluated at the detected ridge points (i.e., equation 13 may be applied by taking the appropriate discrete derivatives of the intensity distribution about the ridge points). Other methods for evaluating the greyscale surface local to detected ridge points may also be used, as the aspect of the invention relating to determining an initial radius estimation is not limited to any particular implementation technique. For example, the distance to an inflection point of the intensity distribution in a direction along the principal direction of curvature (i.e., along the vector $u_0$) about each ridge point may be determined to estimate an initial value for the radius of each cylindrical segment in the model. Thus, in one embodiment, values for the radius parameter (i.e., $r_i$) may be determined from information in the view data.

The orientation of each cylindrical primitive may also be assigned one or more values based on information obtained from the sinogram to further improve the results and constrain the optimization. The orientation of the longitudinal axis of a cylindrical primitive is related to the eccentricity of the elliptical cross-section in a given slice. As shown in FIG. 6, the smaller the angle between the longitudinal axis of the cylinder and the plane of the slice, the greater the eccentricity. At one extreme, the cylindrical axis intersects the plane at a ninety degree angle resulting in an ellipse having an eccentricity of zero (i.e., a circle). At the other extreme, the cylindrical axis is parallel to the plane and a line having an eccentricity approaching infinity results. In one embodiment, the eccentricity may be computed from characteristics of the gray scale distribution in the sinogram using any suitable technique, to estimate an initial value for the orientation of each cylindrical segment in the model configuration.

Figure 15A:
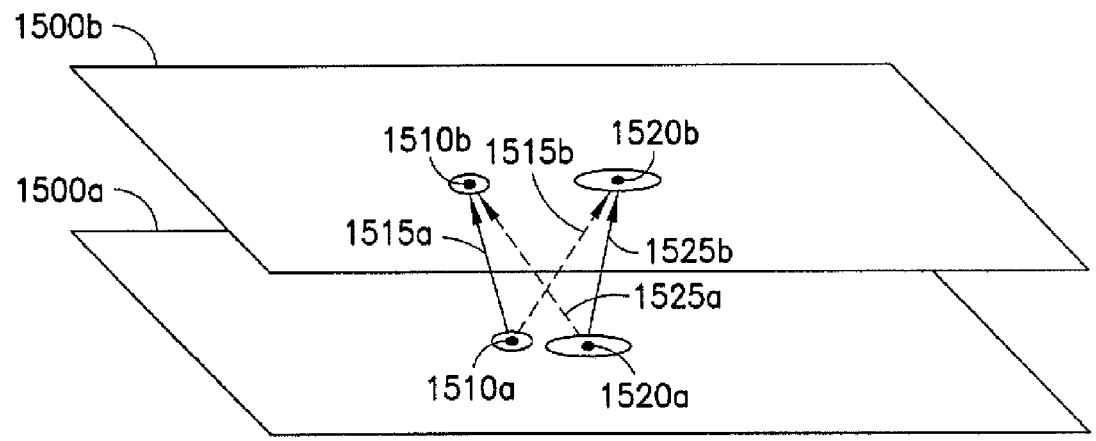
FIG. 15 illustrates a method of determining an orientation and/or a length of cylindrical segments by tracking corresponding locations through a plurality of slices of view data in accordance with one embodiment of the present invention.
Figure 15B:
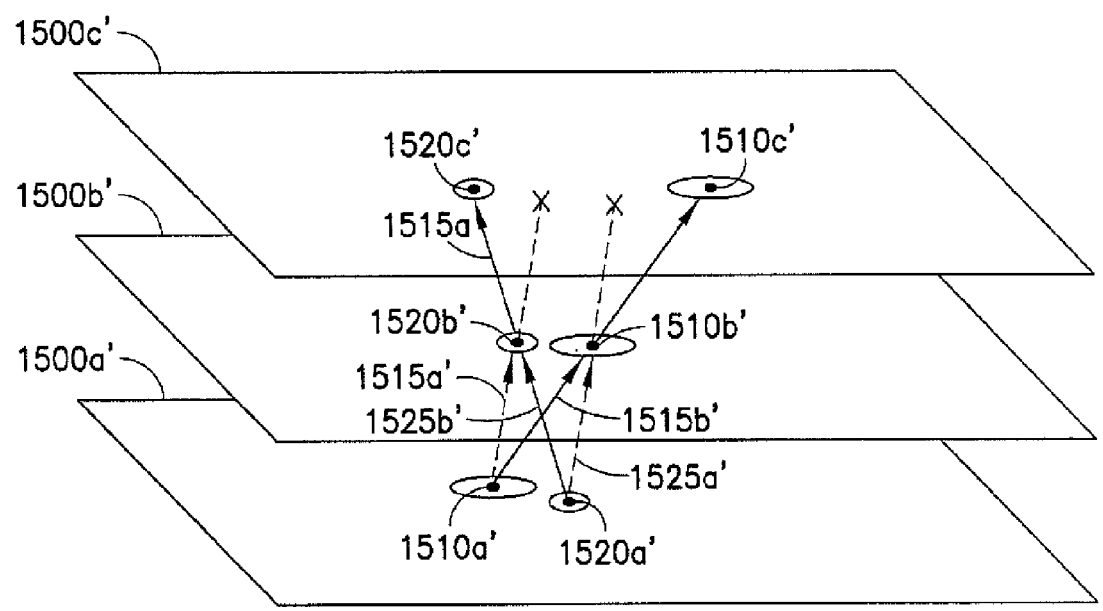

In another embodiment, information across multiple slices (i.e., 3D information) is used to determine cylinder axis orientation, in a manner described referring to FIGS. 15A and 15B. In FIG. 15A, locations 1510a and 1520a were detected as centers of elliptical cross-sections in a slice 1500a, e.g., by detecting and transforming ridge points in the sinogram of the slice as described in acts 332 and 342 in FIG. 14. Similarly, locations 1510b and 1520b were detected as centers of elliptical cross-sections in another slice 1500b. When an ellipse center is detected in one slice, a corresponding ellipse center may be expected in nearby slices to account for the penetration of a cylindrical structure through multiple slices of the scan. The orientation of the cylindrical structure may be estimated from the change in location of the corresponding ellipse centers.

The orientation of each cylindrical primitive may be calculated by choosing a best fit between detected locations in successive slices. For example, a detected location having the shortest vector distance to a detected location in the subsequent slice may be determined to belong to the same cylindrical primitive. In FIG. 15A, location 1510a may be paired with location 1510b since no vector from location 1510a to any other detected location in slice 1500b has a magnitude less than the magnitude of vector 1515a. Similarly, location 1520a may be paired with 1520b. The direction of the vector connecting the paired locations may determine the orientation of the associated cylindrical primitive.

Using the shortest vector method in FIG. 15A, location 1510a' may be incorrectly associated with location 1520b' and location 1520a' may be incorrectly associated with location 1510b'. To avoid this situation, in another embodiment described making reference to FIG. 15B, information in additional slices may be used. For example, the association between 1510a' and 1520b' may be checked against information in slice 1500c'. Since extensions of vectors 1515a' and 1525a' lead to locations where no ellipse centers were detected, the assumption made in the first instance may be penalized to prefer a global best fit, e.g., the grouping of locations 1510a'-1510c' and the grouping of locations 1520a'-1520c'.

The detected locations in any number of slices may be analyzed together to determine the orientation of the various cylindrical primitives in the model configuration. For example, information in a group of N slices may be considered together, e.g., to constrain an optimization, regression and/or statistical scheme to determine the best fit groupings of the detected locations in the N slices. By tracking elliptical cross-section through the various slices, it may be determined when a particular cylinder first appears in a slice and when it terminates. This information may be used to determine the length $l_i$ of each cylindrical segment.

Figure 16:
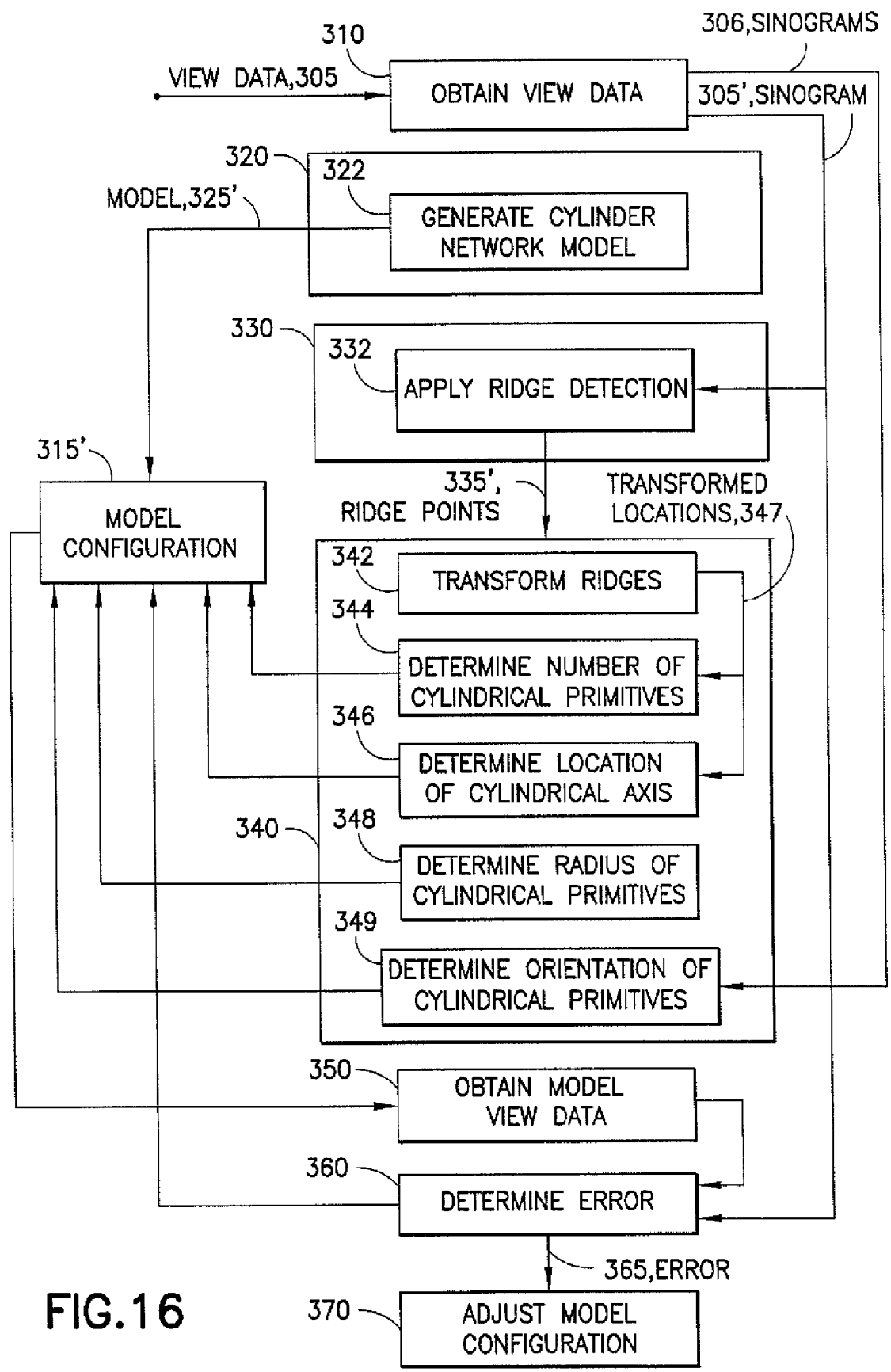
FIG. 16 illustrates a method of determining a number, location, radius and orientation of cylindrical segments in a cylinder network model from features in the view data in accordance with one embodiment of the present invention.

The orientation of the cylindrical primitives may be determined from the observed view data to facilitate a more accurate hypothesis of the initial configuration of the model. For example, FIG. 16 describes an embodiment of a method similar in many ways to the methods described in FIGS. 13 and 14. In FIG. 16, orientation parameters (i.e., $\varnothing_i, \gamma_i$) are also determined from the view data to form the initial hypothesis of model configuration 315'.

In act 349, the orientation of each of the cylindrical primitives 341 detected in act 344 is determined by tracing the locations determined in act 346 through multiple sinograms 306. For example, view data 305 may include view data obtained from multiple slices of the object being scanned (e.g., a pulmonary vessel network). A sinogram may be formed corresponding to each of the slices to form multiple sinograms 306. As discussed above, values for orientation parameters may be estimated by determining a best fit between ellipse centers detected in the multiple sinograms 306.

It should be appreciated that in the embodiment illustrated in FIG. 16, each of the model parameters of the cylindrical segment in FIG. 5A (i.e., $x_i$, $y_i$, $\phi_i$, $\gamma_i$ and $r_i$) is configured based on information obtained from the view data, thus increasing the likelihood that the initial configuration is in the vicinity of the underlying structure and that subsequent optimization (e.g., acts 350-370) will converge to a close approximation of the modeled structure.

In one embodiment, determining initial values for certain parameters may assist in more precisely determining others. For example, determining the orientation of cylindrical primitives in one or more slices may be employed to predict the center location of a corresponding elliptical cross-section in subsequent slices. The location predicted from the orientation may be used as additional information, for example, when determining histogram locations that correspond to true ellipse centers.

In another embodiment, the radius of a cylindrical segment computed for a slice or groups of slices may also be used to predict the radius and guide the computations in subsequent slices and/or may be used to enhance the determination of orientation. In the example in FIG. 15B, if the radii of the respective detected locations were known (or estimated), the possible pairing between location 1510$a'$ and 1520$b'$ may be dispensed with or penalized due to the difference in the radii. In this way, the various model parameters determined from the view data for a slice may not only bootstrap configuring the model for that slice, but may bootstrap determining model parameters in other slices. By utilizing information across slices, a comprehensive regression or other optimization may be implemented to find a best fit configuration in 3D.

In another embodiment, one or more parameters estimated from the view data may be optimized while holding one or more other parameters constant. For example, values for radius parameters of cylindrical primitives identified and positioned in acts 344 and 246 may be approximated by analyzing the greyscale surface features local to the ridge points (e.g., according to equation 13). The configuration may then be optimized for the estimated parameters (e.g., location and radius) while holding orientation parameters constant. For example, for the purposes of the optimization, each identified cylindrical segment may be assigned an orientation such that the cylinder pierces a slice at a ninety degree angle (i.e., the cylindrical cross-section in the plane of the slice is a circle).

This process may be repeated for a plurality of slices. After the estimated parameters (e.g., location and radius) are optimized for multiple slices, the orientation of the cylindrical primitives may be determined by tracing centers of cross-sections of the cylindrical primitives through the plurality of slices (e.g., as discussed in connection with FIGS. 15A and 15B). Once values for the orientation parameters have been estimated, the model configuration may again be optimized to arrive at final model configuration.

It should be appreciated that a model configuration may be optimized for any parameter or combination of parameters, while holding other parameters constant. For example, the model configuration described above may be optimized for the location parameter while holding radius and orientation parameters constant, or any other suitable combination, as the aspects of the invention are not limited in this respect.

The various structures of an object of interest generate projection information that is superpositive in the view data. Certain of these structures may give rise to information in the view data that tends to overpower information related to other structures. For example, at certain views of the object, smaller structure may be partially or entirely occluded by larger structures. As such, the relatively large attenuation caused by the relatively large amount of material being penetrated in the larger structure, when added to the relatively small attenuation due to the smaller structure, tends to wash out the information corresponding to the small structure making it difficult to detect.

Figure 17:
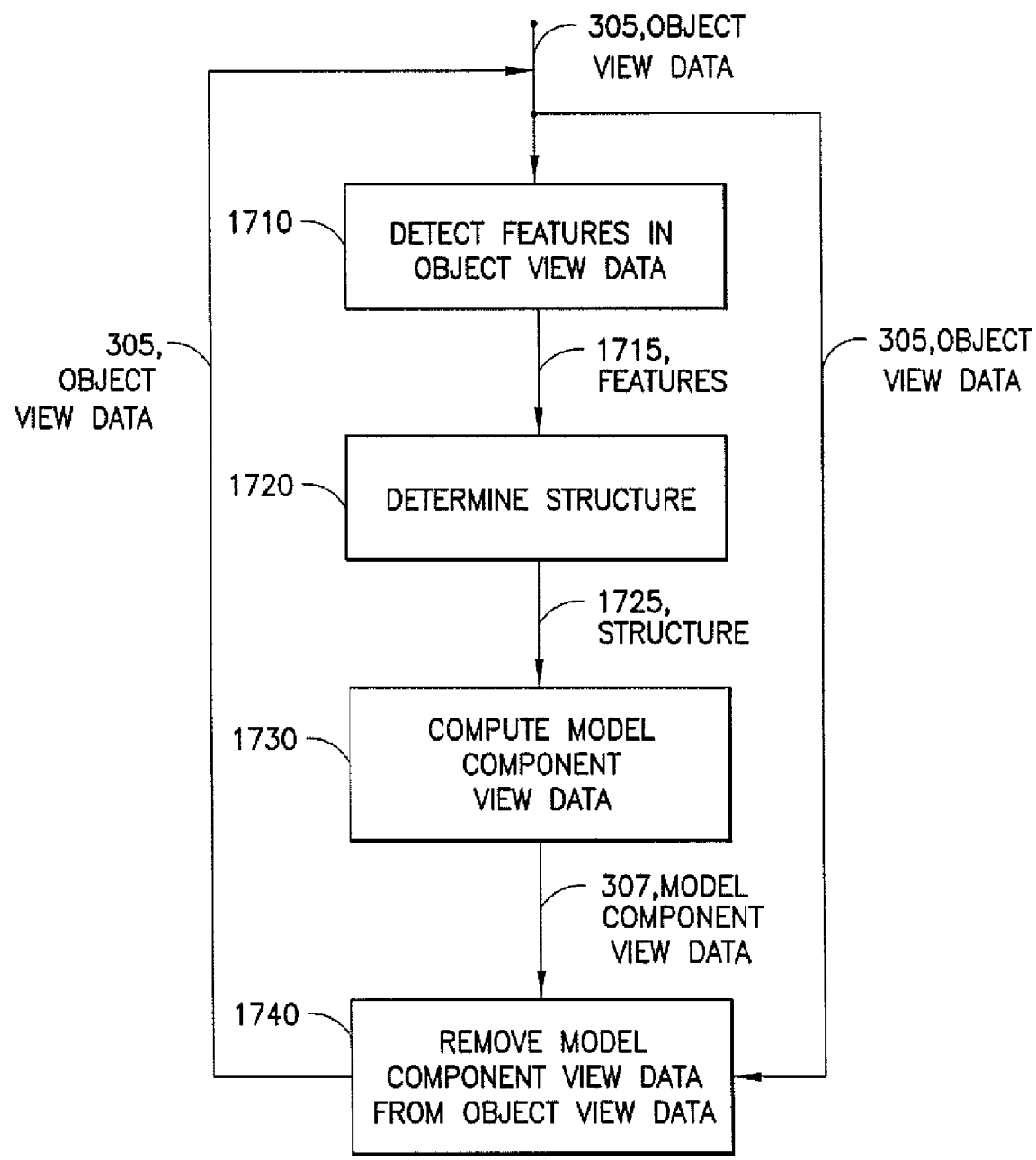
FIG. 17 illustrates a method of iteratively removing features from view data in accordance with one embodiment of the present invention.

FIG. 17 illustrates one embodiment of a method for iteratively processing view data to remove detected features so that previously obscured information may become detectable. In act 1710, the object view data obtained from an object of interest may be processed to detect various features in the data. For example, ridge detection may be applied to one or more sinograms formed from the view data to determine possible axis locations for cylinder primitives in a cylinder network model.

In act 1720, features 1715 detected in the view data may be used to configure one or more component parts of a model. For example, it may be determined that features 1715 correspond to one or more cylindrical primitives in a cylinder network model. Since feature detection is more likely to identify the most salient information, features 1715 may correspond to the most prominent structure in the object of interest. For example, the features may correspond to blood vessels having large diameters in a scan including blood vessel structure.

In act 1730, model component view data may be obtained from the one or more components configured in act 1720. For example, the radon transform may be used to project the configured model components into view space. In act 1470, the model component view data may be subtracted from the object view data to remove the associated features. By removing the features that have already been detected, subsequent feature detection may be more likely to identify features that were buried under more salient information.

This process may be repeated as desired, for example, until a satisfactory amount of structure has been extracted from the sinogram, feature detection fails to identify any additional features, etc. The peeling away of information in the view data may facilitate detection of small dimensioned structure. In addition, by iteratively removing the most salient information, feature detection may be adjusted to make it optimal for each iteration. For example, kernel sizes of differential operators used in locating ridge points may be varied to make them more sensitive to information at a resolution characteristic of a particular iteration. Similarly, threshold values or other criteria may be adjusted or changed to optimize detection of information at a resolution expected of the particular iteration.

It should be appreciated that the view data operated on in methods of the various embodiments described herein may be at the maximum resolution that a given X-ray scanning device can generate. For example, various factors such as the number of detectors in the X-ray scanning device (or the sampling rate of a detector array), the angle interval over which the data is obtained, etc., limit the resolution of the view data. As discussed above, the resolution of the view data exceeds the resolution of images reconstructed from the data. For example, the resolution of the view data may be up to five times the resolution of the reconstructed image data, or more. Accordingly, by operating directly on the view data, various aspects of the invention may facilitate detection of structure at a higher resolution than available by detection methods applied to conventional reconstructed images.

For example, conventional reconstructed images from view data obtained by large object X-ray devices (i.e., devices other than microCT devices, such as those suitable for scanning portions of the human anatomy in situ) may be unable to resolve structure below 500 microns. By detecting structure via direct processing of the view data according to methods of the present invention described herein, structures may be detected having dimensions below 500 microns, more preferably below 250 microns, more preferably below 100 microns, and even more preferably below 50 microns.

As discussed above, microCT may be capable of providing view data at a resolution an order of magnitude or more higher than large object X-ray devices. Conventional reconstructed image from view data obtained by microCT devices may be unable to resolve structure below 50 microns. By detecting structure via direct processing of the view data according to methods of the present invention described herein, structures may be detected below 50 microns, more preferably below 25 microns, more preferably below 10 microns, and even more preferably below 5 microns.

It should be appreciated that optimizing or otherwise updating a configuration via comparisons with the view data is different than detecting features in the view data to determine a value for one or more model parameters. Detecting a feature involves gleaning information directly from the view data itself as opposed to conventional techniques for optimizing a model to view data, whereby any information about the view data is determined indirectly through the use of the model.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that one embodiment of the invention is directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, various aspects of the invention may be used with models of any type to detect any type of feature in the view data and is not limited to any particular model, to modeling any particular type of structure, or to any detecting any particular type of feature, property or characteristic. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method to determine a value for at least one parameter of a configuration of a model that includes a plurality of cylindrical primitives, the model associated with structure of which object view data has been obtained, the object view data including at least one sinogram, the method comprising acts of:

detecting at least one feature in the at least one sinogram including detecting at least one derivative property of the at least one sinogram, at least in part, by computing a Hessian at a plurality of pixels in the at least one sinogram and selecting each of the plurality of pixels wherein the respective Hessian has at least one eigenvalue that meets a predetermined criteria, the location of the selected pixels forming a plurality of ridge points;

determining the value for the at least one parameter of the configuration of the model based, at least in part, on the at least one feature including transforming a location of each of the plurality of ridge points from a coordinate frame of the at least one sinogram to a respective location in a coordinate frame of the model to form a plurality of center locations;

forming a histogram from the plurality of center locations;

determining a number of cylindrical primitives in the configuration of the model based on a number of peaks in the histogram; and determining a location of each of the plurality of cylindrical primitives based on the center locations at the peaks in the histogram including determining an axis location of a cylindrical axis of each of the plurality of cylindrical primitives at an intersection with a plane associated with the at least one sinogram.

2. The method of claim 1, wherein the act of selecting each of the plurality of pixels includes an act of selecting each of the plurality of pixels wherein the respective Hessian has a principal eigenvalue having an absolute value greater than a first predetermined threshold.

3. The method of claim 2, wherein the act of selecting each of the plurality of pixels includes an act of selecting each of the plurality of pixels having a local maximum intensity.

4. A method to determine a value for at least one parameter of a configuration of a model having a plurality of cylindrical primitives, the model associated with structure of which object view data has been obtained, the object view data including at least one sinogram, the method comprising acts of:
    detecting at least one feature in the at least one sinogram including detecting at least one derivative property of the at least one sinogram, at least in part, by computing a Hessian at a plurality of pixels in the at least one sinogram and selecting each at the plurality of pixels wherein the respective Hessian has at least one eigenvalue that meets a predetermined criteria, the location of the selected pixels forming a plurality of ridge points, wherein detecting the at least one feature includes detecting at least one property of the intensity distribution about each of the plurality of ridge points; and
    determining the value for the at least one parameter of the configuration of the model based, at least in part, on the at least one feature including determining a value of a radius of at least one of the plurality of cylindrical primitives based, at least in part, on the at least one property of the intensity distribution.

5. The method of claim 4, wherein the structure includes a blood vessel network, the model includes a plurality of cylindrical segments, and the at least one parameter comprises a number of the plurality of cylindrical segments, a location of each of the plurality of cylindrical segments, a radius for each of the plurality of cylindrical segments, and an orientation of each of the plurality of cylindrical segments, and wherein the act of determining the value of the at least one parameter includes an act of determining the number of the plurality of cylindrical segments, the location, the radius, and the orientation of each of the plurality of cylindrical segments based, at least in part, on the at least one feature.

6. A method to determine a value for at least one parameter of a configuration of a model including a plurality of cylindrical segments, the model associated with structure of which object view data has been obtained, the method comprising acts of:
    detecting at least one feature in the object view data; and
    determining the value for the at least one parameter of the configuration of the model based, at least in part, on the at least one feature, wherein the act of determining the value of the at least one parameter includes an act of determining a value of at least one parameter based, at least in part, on information detected in a plurality of portions of the object view data, each of the plurality of portions obtained from a respective different slice of the structure, each of the plurality of portions of the object view data comprising a sinogram, wherein the act of determining the value of the at least one parameter includes an act of determining at least one orientation parameter by associating together, as part of a cylindrical segment, elliptical cross-sections detected in each sinogram, and wherein the act of determining the value of the least one parameter includes an act of determining an orientation of at least one of the plurality of cylindrical segments based on a direction of a line connecting center locations of the associated elliptical cross-sections.

7. The method of claim 6, wherein the value of the at least one parameter is an initial value, and further comprising acts of:
    transforming the configuration of the model into view space to obtain model view data;
    comparing the model view data to the object view data of the structure to obtain a difference measure; and
    updating the value of at least one of the at least one parameters based on the difference measure to obtain an updated configuration of the model.

8. The method of claim 6, wherein the structure includes at least one blood vessel.

9. The method of claim 6, further comprising an act of providing information about the structure from the configuration of the model.

10. A method to determine a value for at least one parameter of a configuration of a model including a plurality of cylindrical primitives, the model associated with structure of which object view data has been obtained, the object view data including a plurality of sinograms including first and second sinograms, each sinogram associated with a respective slice of the structure, the first portion comprising the first sinogram and the second portion comprising the second sinogram, the method comprising acts of:
    detecting at least one feature in the object view data; and
    determining the value for the at least one parameter of the configuration of the model based, at least in part, on the at least one feature, wherein the act of determining the value of the at least one parameter includes an act of determining a value of at least one parameter based, at least in part, on information detected in a plurality of portions of the object view data, each of the plurality of portions obtained from a respective different slice of the structure, wherein the act of determining the value of the at least one parameter includes an act of determining a value of at least one parameter, at least in part, by determining at least one relationship between first information detected in a first portion of the object view data obtained from a first slice of the structure and second information detected in a second portion of the object view data obtained from a second slice of the structure, wherein the act of determining the at least one relationship includes an act of determining a relationship between a first transformed location of at least one first characteristic point in the first sinogram and a second transformed location of at least one second characteristic point in the second sinogram including determining a vector direction from the first transformed location to the second transformed location including determining a value for at least one orientation parameter of the configuration of the model based on the vector direction including a value of an orientation of at least one of the plurality of cylindrical primitives based on the vector direction including acts of;
    determining a first axis location of one of the plurality cylindrical primitives at a first slice corresponding to the first sinogram based on the first transformed location; and determining a second axis location of one of the plurality of cylindrical primitives at a second slice corresponding to the second sinogram based on the second transformed location.

11. The method of claim 10, wherein the act of determining the value of the orientation includes an act of determining a value of at least one orientation of at least one of the plurality of cylindrical primitives based on a direction of a connecting line between the first axis location and the second axis location.

12. A method to determine a value for at least one parameter of a configuration of a model, the model associated with structure of which object view data has been obtained, the object view data including a plurality of sinograms including first and second sinograms, each sinogram associated with a respective slice of the structure, the first portion comprising the first sinogram and the second portion comprising the second sinogram, the method comprising acts of;
detecting at least one feature in the object view data including detecting a plurality of ridge points;
transforming a location of each of the plurality of ridge points in view space to determine a plurality of center locations in model space;
determining the value for the at least one parameter of the configuration of the model based, at least in part, on the at least one feature, wherein the act of determining the value of the at least one parameter includes an act of determining a value of at least one parameter based, at least in part, on information detected in a plurality of portions of the object view data, each of the plurality of portions obtained from a respective different slice of the structure, wherein the act of determining the value of the at least one parameter includes an act of determining a value of at least one parameter, at least in part, by determining at least one relationship between first information detected in a first portion of the object view data obtained from a first slice of the structure and second information detected in a second portion of the object view data obtained from a second slice of the structure, wherein the act of determining the at least one relationship includes an act of determining a relationship between a first transformed location of at least one first characteristic point in the first sinogram and a second transformed location of at least one second characteristic point in the second sinogram, the value of the at least one parameter being based on the at least one relationship; and
grouping together the plurality of center locations into a plurality of associated groups, each center location in an associated group corresponding to a respective different one of the plurality of sinograms, each group further associated with a respective one of the plurality of cylindrical primitives.

13. The method of claim 12, wherein the act of grouping together center locations includes an act of grouping center locations such that lines connecting the center locations in each respective group meet a best fit criteria.

14. The method of claim 13, wherein the act of determining the value for at least one orientation includes an act of assigning the vector direction of the line connecting the center locations in a group to an orientation parameter of the associated cylindrical primitive.

15. A computer readable medium encoded with a program for execution on at least one processor, the program, when executed on the at least one processor, performing a method to determine a value for at least one parameter of a configuration of a model including a plurality of cylindrical primitives, the model associated with structure of which object view data has been obtained, the object view data including at least one sinogram, the method comprising acts of:
detecting at least one feature in the object view data including detecting at least one feature in the at least one sinogram, wherein the act of detecting the at least one feature includes an act of detecting at least one derivative property of the sinogram including an act of computing a Hessian at a plurality of pixels in the at least one sinogram including an act of selecting each of the plurality of pixels wherein the respective Hessian has at least one eigenvalue that meets a predetermined criteria, the location of the selected pixels forming a plurality of ridge points; and
determining the value for the at least one parameter of the configuration of the model based, at least in part, on the at least one feature including an act of transforming a location of each of the plurality of ridge points from a coordinate frame of the at least one sinogram to a respective location in a coordinate frame of the model to form a plurality of center locations;
forming a histogram from the plurality of center locations;
determining a number of cylindrical primitives in the configuration of the model based on a number of peaks in the histogram;
determining a location of each of the plurality of cylindrical primitives based on the center locations at the peaks in the histogram; and
determining an axis location of a cylindrical axis of each of the plurality of cylindrical primitives at an intersection with a plane associated with the at least one sinogram.

16. A computer readable medium encoded with a program for execution on at least one processor, the program, when executed on the at least one processor, performing a method to determine a value for at least one parameter of a configuration of a model, the model associated with structure of which object view data has been obtained, the object view data including at least one sinogram, the method comprising acts of:
detecting at least one feature in the object view data including detecting at least one feature in the at least one sinogram, wherein the act of detecting the at least one feature includes an act of detecting at least one derivative property of the sinogram including an act of computing a Hessian at a plurality of pixels in the at least one sinogram including an act of selecting each of the plurality of pixels wherein the respective Hessian has at least one eigenvalue that meets a predetermined criteria, the location of the selected pixels forming a plurality of ridge points, wherein the act of detecting the at least one feature includes an act of detecting at least one property of the intensity distribution about each of the plurality of ridge points; and
determining the value for the at least one parameter of the configuration of the model based, at least in part, on the at least one feature including an act of determining a value of a radius of at least one of the plurality of cylindrical primitives based, at least in part, on the at least one property of the intensity distribution.

17. The computer readable medium of claim 16, wherein the structure includes at least one blood vessel.

18. The computer readable medium of claim 16, wherein the structure includes a blood vessel network, the model includes a plurality of cylindrical segments, and the at least one parameter comprises a number of the plurality of cylindrical segments, a location of each of the plurality of cylindrical segments, a radius for each of the plurality of cylindrical segments, and an orientation of each of the plurality of cylindrical segments, and wherein the act of determining the value of the at least one parameter includes an act of determining the number of the plurality of cylindrical segments, the location, the radius, and the orientation of each of the plurality of cylindrical segments based, at least in part, on the at least one feature.

19. A computer readable medium encoded with a program for execution on at least one processor, the program, when executed on the at least one processor, performing a method to determine a value for at least one parameter of a configuration of a model including a plurality of cylindrical segments, the model associated with structure of which object view data has been obtained, the method comprising acts of:
  detecting at least one feature in the object view data; and
  determining the value for the at least one parameter of the configuration of the model based, at least in part, on the at least one feature including an act of determining a value of at least one parameter based, at least in part, on information detected in a plurality of portions of the object view data, each of the plurality of portions of the object view data comprises a sinogram, each of the plurality of portions obtained from a respective different slice of the structure, wherein the act of determining the value of the at least one parameter includes an act of associating together, as part of a cylindrical segment, elliptical cross-sections detected in each sinogram, and wherein the act of determining the value of the least one parameter includes an act of determining an orientation of at least one of the plurality of cylindrical segments based on a direction of a line connecting center locations of the associated elliptical cross-sections.

20. The computer readable medium of claim 19, wherein the structure includes at least one blood vessel and the object view data comprises object view data obtained from a scan of the at least one blood vessel, further comprising an act of updating the model configuration according to a comparison with the object view data to arrive at a final model configuration, so that the final model configuration represents the at least one blood vessel.

21. The computer readable medium of claim 20, wherein the at least one feature includes one or more derivative properties and the model includes a plurality of primitives, and wherein the act of determining the value of at least one parameter includes an act of determining a number of primitives in the model configuration and a location for at least one of the plurality of primitives based, at least in part, on a set of characteristic points in the object view data exhibiting the one or more derivative properties.

22. The computer readable medium of claim 21, wherein the act of determining the location includes an act of determining a location of each of the plurality of primitives based on a transformation of locations of the set of characteristic points into a coordinate frame of the model.

23. The computer readable medium of claim 22, wherein the plurality of primitives comprise cylindrical segments and the object view data includes a plurality of sinograms corresponding to a respective plurality of slices of the at least one blood vessel, and wherein the act of determining the location of each of the plurality of primitives includes an act of determining, for each of the cylindrical segments, a center of a cross-section of the cylinder segment in a plane corresponding to at least one of the slices.

24. The computer readable medium of claim 23, wherein the at least one feature includes an intensity distribution about at least some of the set of characteristic points, and wherein the act of determining the value includes an act of determining a radius of at least one of the plurality of cylindrical segments based on the intensity distribution.

25. The computer readable medium of claim 23, wherein the act of determining the value of the at least one parameter includes an act of determining an orientation for at least one of the cylindrical segments by computing a direction of a line connecting the centers of the cross-sections of at least two cylindrical segments in planes corresponding to at least two of the plurality of sinograms.

26. The computer readable medium of claim 20, wherein the act of updating the model configuration includes acts of;
  obtaining model view data from the model configuration;
  comparing the object view data and the model view data to obtain an error value; and
  modifying at least one of the plurality of parameters describing the model configuration to reduce the error value.

27. The computer readable medium of claim 26, wherein the act of updating the model configuration includes an act of iteratively updating the model configuration to achieve a least squares fit between the model view data and the object view data.

28. The computer readable medium of claim 19, wherein the structure includes a plurality of blood vessels, the object view data comprises object view data obtained from scanning the plurality of blood vessels, and the model includes a plurality of model components, and wherein the act of determining a value for the at least one parameter includes acts of:
  determining a configuration of at least one first model component based, at least in part, on the at least one feature, the at least one first model component representing at least one of the plurality of blood vessels;
  removing information in the object view data corresponding to the at least one blood vessel as represented by the at least one first model component; and
  determining a configuration of at least one second model component, based at least in part, on at least one feature detected in the object view data after the act of removing information.

29. The computer readable medium of claim 28, wherein the act of removing information includes an act of obtaining model component view data corresponding to the configuration of the at least one first model component.

30. The computer readable medium of claim 29, wherein the act of removing information includes an act of subtracting the model component view data from the object view data 31. A computer readable medium encoded with a program for execution on at least one processor, the program, when executed on the at least one processor, performing a method to determine a value for at least one parameter of a configuration of a model including a plurality of cylindrical primitives, the model associated with structure of which object view data has been obtained, the object view data including a plurality of sinograms including first and second sinograms, each sinogram associated with a respective slice of the structure, the first portion comprising the first sinogram and the second portion comprising the second sinogram, the method comprising acts of:
  detecting at least one feature in the object view data; and
  determining the value for the at least one parameter of the configuration of the model based, at least in part, on the at least one feature including an act of determining a value of at least one parameter based, at least in part, on information detected in a plurality of portions of the object view data, each of the plurality of portions obtained from a respective different slice of the structure, wherein the act of determining the value of the at least one parameter includes an act of determining a value of at least one parameter, at least in part, by determining at least one relationship between first information detected in a first portion of the object view data obtained from a first slice of the structure and second information detected in a second portion of the object view data obtained from a second slice of the structure, wherein the act of determining the at least one relationship includes an act of determining a relationship between a first transformed location of at least one first characteristic point in the first sinogram and a second transformed location of at least one second characteristic point in the second sinogram including an act of determining a vector direction from the first transformed location to the second transformed location and determining a value for at least one orientation parameter of the configuration of the model based on the vector direction including determining a value of an orientation of at least one of the plurality of cylindrical primitives based on the vector direction, the value of the at least one parameter being based on the at least one relationship, wherein the act of determining the value for the at least one parameter includes acts of:

determining a first axis location of one of the plurality cylindrical primitives at a first slice corresponding to the first sinogram based on the first transformed location; and determining a second axis location of one of the plurality of cylindrical primitives at a second slice corresponding to the second sinogram based on the second transformed location.

32. The computer readable medium of claim 31, wherein the act of determining the value of the orientation includes an act of determining a value of at least one orientation of at least one of the plurality of cylindrical primitives based on a direction of a connecting line between the first axis location and the second axis location.

* * * * *